US011039811B2

(12) United States Patent
Degertekin et al.

(10) Patent No.: US 11,039,811 B2
(45) Date of Patent: Jun. 22, 2021

(54) MRI COMPATIBLE 3-D INTRACARDIAC ECHOGRAPHY CATHETER AND SYSTEM

(71) Applicants: Georgia Tech Research Corporation, Atlanta, GA (US); The United States of America, As Represented by the Secretary, Department of Health and Human Services, Bethesda, MD (US)

(72) Inventors: Fahrettin Levent Degertekin, Atlanta, GA (US); Coskun Tekes, Alpharetta, GA (US); Robert Jay Lederman, Chevy Chase, MD (US); Ozgur Kocaturk, Bethesda, MD (US); M. Wasequr Rashid, Atlanta, GA (US); Maysam Ghovanloo, Atlanta, GA (US)

(73) Assignees: Georgia Tech Research Corporation, Atlanta, GA (US); The United States of America, as Represented by The Secretary, Department of Health and Human Services, Bethesda, MD (US)

( * ) Notice: Subject to any disclaimer, the term of this patent is extended or adjusted under 35 U.S.C. 154(b) by 320 days.

(21) Appl. No.: 16/178,665

(22) Filed: Nov. 2, 2018

(65) Prior Publication Data
US 2019/0090841 A1    Mar. 28, 2019

Related U.S. Application Data

(63) Continuation of application No. 15/024,995, filed as application No. PCT/US2014/057506 on Sep. 25, 2014, now Pat. No. 10,123,768.
(Continued)

(51) Int. Cl.
*A61B 8/00* (2006.01)
*A61B 8/08* (2006.01)
(Continued)

(52) U.S. Cl.
CPC ............... *A61B 8/12* (2013.01); *A61B 1/05* (2013.01); *A61B 8/0883* (2013.01); *A61B 8/445* (2013.01);
(Continued)

(58) Field of Classification Search
CPC ............... G01S 7/5208; G01S 15/8913; G01S 7/52034; G01S 15/8925; B06B 1/0292;
(Continued)

(56) References Cited

U.S. PATENT DOCUMENTS 10,123,768 B2 * 11/2018 Degertekin .............. A61B 1/05
2003/0216642 A1   11/2003 Pepin et al.
(Continued)

OTHER PUBLICATIONS

Daft, et al., "Two Approaches to Electronically Scanned 3D Imaging Using cMUTs," IEEE Ultrasoncis Symposium 2006, pp. 685-688; Mountain View, California.
(Continued)

*Primary Examiner* — Daniel Pihulic
(74) *Attorney, Agent, or Firm* — Troutman Pepper Hamilton Sanders LLP; Ryan A. Schneider

(57) ABSTRACT

An intracardiac imaging system has an MRI compatible intracardiac echography catheter having transmitters, receivers, a multiplexer, and a beamformer. The catheter can include an atraumatic tip disposed on the distal end of the catheter, a pair of inductively coupled coils proximal the atraumatic tip, at least one CMUT-on-CMOS volumetric imaging chip disposed between the pair of coils, and a cable lumen disposed within the volume sized to house a small number of electrical connections due to significant multiplexing in the CMUT-on-CMOS chip. The catheter can be made of MRI compatible materials and can include active cooling channels.

20 Claims, 20 Drawing Sheets

Related U.S. Application Data

(60) Provisional application No. 61/882,371, filed on Sep. 25, 2013.

(51) Int. Cl.
   *A61B 8/12* (2006.01)
   *A61B 1/05* (2006.01)
   *G01S 15/89* (2006.01)
   *G01S 7/52* (2006.01)
   *B06B 1/02* (2006.01)

(52) U.S. Cl.
   CPC .............. *A61B 8/56* (2013.01); *G01S 7/5208* (2013.01); *G01S 15/8913* (2013.01); *A61B 8/4254* (2013.01); *A61B 8/546* (2013.01); *B06B 1/0292* (2013.01); *G01S 7/52034* (2013.01); *G01S 15/8925* (2013.01)

(58) Field of Classification Search
   CPC ........... A61B 8/12; A61B 8/0883; A61B 8/56; A61B 1/05; A61B 8/445; A61B 8/4254; A61B 8/546
   See application file for complete search history.

(56) References Cited

U.S. PATENT DOCUMENTS

| | | |
|---|---|---|
| 2004/0152437 A1 | 8/2004 | Behzad |
| 2005/0146247 A1 | 7/2005 | Fisher et al. |
| 2007/0167812 A1 | 7/2007 | Lemmerhirt et al. |
| 2008/0275395 A1 | 11/2008 | Asbury et al. |
| 2010/0036284 A1 | 2/2010 | Laynes et al. |
| 2010/0152590 A1 | 6/2010 | Moore et al. |
| 2010/0317962 A1 | 12/2010 | Jenkins et al. |
| 2011/0087104 A1 | 4/2011 | Moore et al. |
| 2012/0257690 A1 | 10/2012 | Li et al. |
| 2013/0064043 A1 | 3/2013 | Degertekin et al. |
| 2019/0090841 A1* | 3/2019 | Degertekin .............. A61B 8/12 |

OTHER PUBLICATIONS

Search Report and Written Opinion from EP Application No. EP14849842 dated Feb. 28, 2017 (6 pages).

International Search Report and Written Opinion in PCT Application No. PCT/US2014/057506, dated Dec. 18, 2014.

* cited by examiner

|  | ICE 1 | ICE 2 | ICE 3 |
|---|---|---|---|
| ARRAY CONFIGURATION: PERIPHERAL Rx ARRAY CENTRAL Tx ARRAYS | | | |
| ARRAY SIZE | 7 x 2.8 mm | 7 x 2.8 mm | 7 x 2.8 mm |
| # OF Rx ELEMENTS | 192 | 192 | 192 |
| # OF Tx ELEMENTS | 15 DEFOCUSED/FOCUSED RECTANGULAR RINGS | 40 CODED ELMS WITH 4 DEFOCUSED/FOCUSED SUB ELMS | 16 LINEAR ARRAY (32 ELMS EACH) |
| CENTER FREQUENCY | 10 MHz | 10 MHz | 10 MHz |
| FRAC. BANDWIDTH | 80% | 80% | 80% |
| ELEMENT PITCH | 100 μm IN Rx | 100 μm IN Rx | 100 μm IN Rx |
| IMAGING DEPTH | 5-15 cm | 5-15 cm | 5-15 cm |
| LATERAL RESOLUTION @ 5cm | 2.1mm | 1.25mm | 1.25mm |
| AXIAL RESOLUTION | 100 μm (IDEAL) | 100 μm (IDEAL) | 100 μm (IDEAL) |
| VIEW ANGLE @ 5cm | 90° x 90° | 90° x 90° | 90° x 90° |
| # OF FIRINGS | 1 | 1-2 WITH CODING | 90 FIRINGS WITH CODING 1 2D PLANE/FIRING |
| VOLUMETRIC FRAME RATE (fps) | 20 | 20 | 20 |
| INTER FOCUS DISTANCE ($\lambda/5$) | 30 μm | 30 μm | 30 μm |
| # OF FOCAL PTS / BEAM | 1600 | 1600 | 1600 |
| # OF BEAMS / VOL. | 90x90=8100 | 90x90=8100 | 90x90=8100 |
| RECON. PIXELS / VOL. | 12M | 12M | 12M |
| RECON. VOXELS / SEC | 240M | 240M | 240M |
| BEAMFORMING OPERATIONS / 3D FRAME | 2.3G | 92G | 207G |
| BEAMFORMING OPERATIONS / SEC | 46G | 1840G | 4140G |

FIG. 2

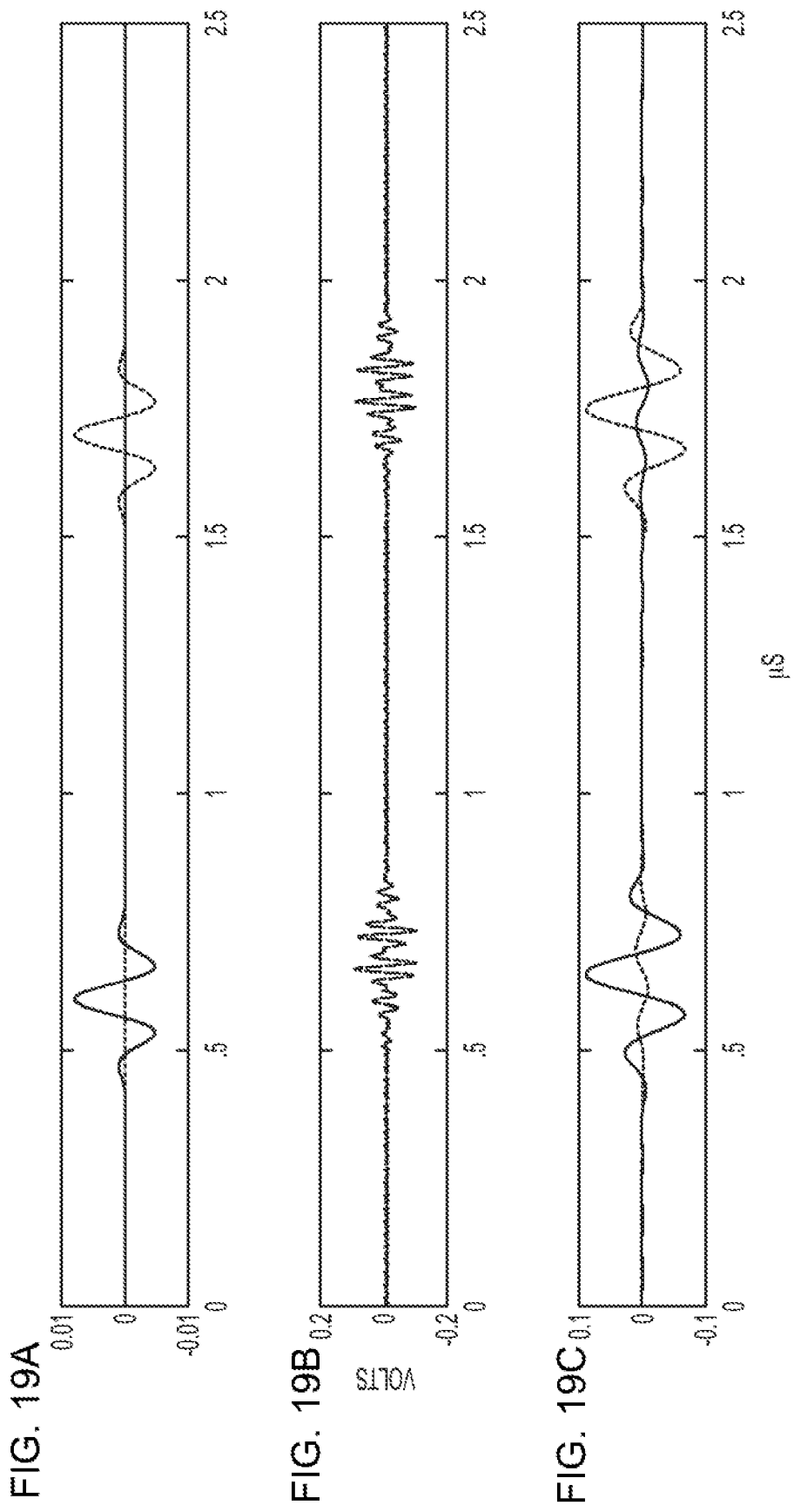

US 11,039,811 B2

MRI COMPATIBLE 3-D INTRACARDIAC ECHOGRAPHY CATHETER AND SYSTEM

CROSS-REFERENCE TO RELATED APPLICATIONS

This application is a continuation of U.S. patent application Ser. No. 15/024,995, filed 25 Mar. 2016, which is the National Stage of International Patent Application PCT/US2014/057506, filed 25 Sep. 2014, and which further claims priority to U.S. Provisional Application Ser. No. 61/882,371 filed 25 Sep. 2013. The entirety of each of these applications is incorporated herein by reference.

STATEMENT REGARDING FEDERALLY SPONSORED RESEARCH OR DEVELOPMENT

This invention was made with government support with Grant No. EB010070 awarded by National Institutes of Health. The government has certain rights in the invention.

BACKGROUND OF THE INVENTION

1. Field of Invention

The invention related to a system for intracardiac imaging with an intracardiac echography catheter. The catheter includes transmitting elements transmitting an imaging pulse, receiving elements, disposed in proximity to at least a portion of the transmitting elements, receiving the imaging pulse, and at least a portion of the receiving elements each generating a receiver signal, and electronics interfacing with at least a portion transmitting elements and at least a portion receiving elements including a multiplexing component receiving at least a portion of the generated receiver signals simultaneously and reducing a number of output signals, based on the receiver signals, by a ratio of between 15-to-1 and 50-to-1, and a beamforming component communicating with at least a portion of the transmitting elements.

The catheter can utilize capacitive micromachined ultrasonic transducer ("CMUT") on complementary metal-oxide-semiconductor ("CMOS") technology for volumetric ultrasound imaging. The catheter can be operated in an MRI system as well as in an X-Ray system to guide intracardiac interventions in real time.

2. Background and Related Art

Symptomatic adult and pediatric structural heart disease (such as valvular heart disease or cardiac septal defects) affects more than 2.9% of the US population, not including cardiomyopathies and rhythm disorders. Because of procedural morbidity, only a minority are selected for surgical relief of symptoms. Nonsurgical repair of structural heart disease is possible using image guidance and newer devices such as transcatheter aortic valves, mitral valve repairs, and intracardiac occluders. Most are guided by X-ray fluoroscopy and adjunctive 2D intracardiac or 3D transesophageal echocardiography ("TEE"). While available transesophageal and intracardiac echo systems are suitable to assess target pathology immediately before and after treatment, they are unsuitable to guide catheter manipulations during therapeutic procedures.

Catheters and target pathology constantly move outside the 2D slices and limited 3D volumes depicted by current echo systems, which also are constrained by interposed lung and bone or by esophageal access route. As a result, operators are forced to use X-ray fluoroscopy to guide catheter manipulation in contemporary repair of complex atrial and ventricular septal defects, valve leaflets, valve replacement, paravalvular leak, and left atrial appendage closure; operators must struggle visually to integrate 2D images into a mental image of anatomic context during key steps of protracted and occasionally unsuccessful procedures. Moreover, current 3D TEE probes, although shown to be useful in repair of septal defects, are not small enough for young children. Miniaturization of ultrasound probes to provide uninterrupted real-time full-volume intraprocedural three-dimensional en face depiction of cardiac pathology and catheter devices would represent a dramatic advance in image-guided intervention

BRIEF SUMMARY OF THE INVENTION

Briefly described, in a preferred form, the present invention is an ultrasound imaging catheter comprising transmitting elements transmitting an imaging pulse, receiving elements, disposed in proximity to at least a portion of the transmitting elements, receiving the imaging pulse, and at least a portion of the receiving elements each generating a receiver signal, and electronics interfacing with at least a portion transmitting elements and at least a portion receiving elements comprising a multiplexing component receiving at least a portion of the generated receiver signals simultaneously and reducing a number of output signals, based on the receiver signals, by a ratio of between 15-to-1 and 50-to-1, and a beamforming component communicating with at least a portion of the transmitting elements.

The multiplexing component can use frequency division multiplexing ("FDM").

The multiplexing component can produce the output signals using time division multiplexing ("TDM").

The multiplexing component can use orthogonal frequency division multiplexing ("OFDM").

The multiplexing component can reduce the number of output signals, based on the receiver signals, by a ratio of at least 16-to-1.

The beamforming component can comprise a pulser electrically connected to at least a portion the transmitting elements and a timing and coding circuit electrically connected to the pulser.

The multiplexing component can comprise a feedback transimpedance amplifier ("TIA") receiving receiver signals from at least a portion of the receiving elements, a mixer receiving a first signal from the TIA, a band pass filter ("BPF") receiving a second signal from the mixer, an adder receiving a third signal from the BPF, and a buffer receiving a fourth signal from the adder and producing the output signals.

The multiplexing component can comprise a feedback TIA receiving receiver signals from at least a portion of the receiving elements, a time-gain compensation ("TGC") circuit receiving a first signal from the TIA, a TDM switch receiving a second signal from the TGC, and a buffer receiving a third signal from the TDM switch and producing the output signals.

The multiplexing component can comprises a feedback TIA receiving receiver signals from at least a portion of the receiving elements, a single to differential converter ("STD") receiving a first signal from the TIA, a low band pass filter ("LPF") receiving a second signal from the STD, a mixer receiving a third signal from the LPF, a BPF receiving a fourth signal from the mixer, and a buffer receiving a fifth signal from an adder and producing the output signals.

The TDM switch can sample the second signal at a rate greater than the Nyquist rate.

The electronics can comprise a de-multiplexer receiving the output signals and a filter receiving a first signal from the de-multiplexer and outputting a non-combined output signal.

A first CMUT-on-CMOS chip can comprise the transmitting elements, the receiving elements, and the electronics.

The first CMUT-on-CMOS chip can have the transmitting elements comprise CMUT transmit ("Tx") elements, and the receiving elements comprise CMUT receive ("Rx") elements.

All of the CMUT receive ("Rx") elements can be disposed in proximity to all of the Tx elements, each Rx element generating a receiver signal, the electronics interfacing with all of the Tx elements and the Rx elements, the multiplexing component receiving at least half of the generated receiver signals simultaneously and reducing a number of output signals, based on the receiver signals, by a ratio of between 15-to-1 and 50-to-1, and the beamforming component communicating with all of the Tx elements.

A first CMUT-on-CMOS chip can comprise at least a portion of the transmitting elements, from none to all of the receiving elements, and from none to all the electronics, and wherein a second CMUT-on-CMOS chip comprises the balance of transmitting elements, receiving elements, and electronics not comprising the first CMUT-on-CMOS chip, wherein the second CMUT-on-CMOS chip is separate from the first CMUT-on-CMOS chip, and the chips in a stacked configuration.

The present invention has a goal to dramatically enhance image guidance of complex catheter-based cardiovascular treatments, to avoid radiation exposure especially in children, to allow current procedures to be performed more safely and efficiently, and to enable novel procedures that otherwise might require surgical repair. Common procedures such as ASD closure, and emerging procedures such as closure of ventricular septal defects and paravalvular leak, future repair of valve leaflets, transcatheter valve replacement, and emerging left atrial appendage closures can be difficult, protracted, or unsuccessful because of limitations of available interventional catheter devices but also because of inadequate image guidance.

Commercially available 2D and limited-volume 3D intracardiac ultrasound catheters do not provide suitable full-volume en face images to depict complex cardiac structures in real time, do not adequately depict real-time navigation of catheter tips and shafts, and require adjunctive X-ray guidance. Several 3D catheters with 2D arrays under development use over 200 electrical connections limiting size and flexibility and prohibiting operation under MRI (magnetic resonance imaging). Disclosed below is the capability to build an ultra-miniature ultrasound system-on-a-chip that provides real-time full-volume 3D ultrasound with very few external electrical connections. This can be implemented as a low profile steerable intracardiac catheter and that further can be implemented by design for operation under either MRI or X-ray.

To reach this goal, one advance is MRI catheterization as a radiation-free alternative to X-ray. However, this trades the safety of lower radiation emissions at the expense of real-time spatial resolution. An intracardiac echography ("ICE") operation during MRI can dramatically advance or even revolutionize the capabilities of transcatheter therapy by enabling completely radiation-free non-surgical catheter navigation, depiction of anatomic context, device repair, novel procedures, and assessment of success and complications, in children and adults.

Full volumetric ICE poses significant challenges even apart from MRI safe operation. Ideally, a fully populated 2D matrix phased array with 100 μm×100 μm or smaller elements should be used for 3D ICE. Traditional designs require large numbers of transmission cables, which cause a number of difficulties. Some of the problems are, prohibitive manufacturing complexity and cost, prohibitive form factor for intracardiac catheters, and (incidentally) increased propensity to RF (radio frequency)-induced heating of metal conductors during an MRI.

The tight space constraints of ICE catheters can also preclude integration of electronics with conventional 1D or 2D matrix piezoelectric arrays needed to improve the signal-to-noise ratio ("SNR") and to implement microbeam former concepts and thereby enable 3D TEE probes. This leaves motor driven 1D arrays or swept aperture techniques as the only available alternative without increasing the cable count, and such systems suffer from inadequate view angles and large slice thickness in the elevation direction.

Piezoelectric micromachined ultrasonic transducer ("pMUT") and CMUT technologies provide more robust fabrication methods for 2D matrix arrays as compared with traditional piezoelectrics and both have been shown to have adequate performance for volumetric imaging with approximately 200 elements and same number of cables. Ring annular array structures further reduce the element count and can still provide 3D image guidance, for example along with integrated RF ablation capability. However, such implementations have small active array areas, exacerbating the compromise between penetration depth and tolerance to tissue motion which is critical in ICE.

In all these approaches, even when flip-chip technology and complex through-silicon electrical connections are used for CMUT ring array-CMOS electronics integration. Each array element is still connected to the imaging system with a separate cable resulting in a catheter with more than 70 cables. Therefore, real-time 3D ICE implementation, which requires full volumetric data collection from less than 10 array transmit firings due to fast tissue motion and miniaturization-driven reduction in the number of data transmission lines, requires a different level of system complexity implemented at the catheter tip, even apart from the requirements of MRI safety Low temperature fabrication can be used to build CMUT arrays on the same silicon substrate as the CMOS electronics. This approach, called CMUT-on-CMOS, enables integration of full 3D transmit and low noise receive frontend electronics as well as RF output multiplexing on a single silicon chip to reduce the cable count. An example of this technology utilized in the present invention can achieve thermal mechanical noise limited detection and real-time 3D imaging at 20 MHz with a 1.4 mm diameter 104 element ring array with only 13 electrical connections.

As with other ring arrays, that particular system also presented a tradeoff between motion artifacts and penetration depth. Penetration depth can be improved by utilizing a larger transmit array area available for a side looking 3D ICE array and implementing on-chip coded excitation schemes as discussed below. By massive on-chip multiplexing of high SNR receive signals over a few cables, image data acquisition time can be reduced a few firings to minimize motion artifacts. Therefore, a CMUT-on-CMOS approach, along with innovative on-chip beamforming and massive multiplexing, provides a beneficial platform for full-volume real-time 3D ICE.

If utilizing CMUT-on-CMOS technology, it is used to integrate transmit (Tx) electronics into the catheter tip and heavily multiplexing the receive (Rx) elements. This results in a catheter with small number of cables significantly reducing the heating of the catheter under large RF signals used for MRI. Reduction of number of cables also reduces the cross-sectional area required for electrical connections and makes room for active cooling of the catheter. The catheter also has integrated markers for tracking its position under MRI.

The expected benefits of MRI plus ICE guided structural heart interventional procedures are manifold. Enhanced visualization promises to simplify and shorten current procedures to enhance success, reduce complications, and reduce cost. Enhanced guidance combined with newer devices can enable catheter alternatives to surgery such as non-surgical extra-anatomic bypass (e.g., Glenn shunt, modified Blalock-Taussig shunt) to reduce the steps of Norwood palliation; simplified repair of multifenestrated muscular and of membranous ventricular septal defect by virtue of en-face imaging during device manipulation; leaflet grasping procedures for neochordal implantation to treat degenerative and functional mitral valve regurgitation; and leaflet or annular or subvalvar plication or augmentation of the mitral and tricuspid valves. At present all of these procedures are challenging or unrealistic absent direct surgical visualization. Supine 3D TEE for procedure guidance usually requires prolonged and costly general anesthesia; intracardiac 3D ICE can avert this need and thereby reduce staffing cost (by 1-2 physicians) and risk. En-face imaging of an atrial septal defect ("ASD") potentially may enhance sizing for device selection to avert rare but catastrophic erosion after implantation of an Amplatzer Septal Occluder, and of dynamic sizing of the ostium of the left atrial appendage may overcome the limitations of available alternatives including 3D TEE.

The 3D real-time full-volume MRICE catheter can, for the first time, allow routine ultrasound guidance of catheter manipulation during procedures rather than just inspecting the baseline pathology and results of repair. It can allow universal real-time en-face depiction of target pathology without the constraints of bone and lung windows (transthoracic) and limited probe positioning (transesophageal) in current technology. For the first time it can enable completely radiation-free catheter navigation and depiction of larger anatomic context and tissue characterization using real-time MRI instead of X-ray for catheter navigation. Even without operation under MRI, real-time full volume 3 DICE with higher probe frequency would represent a fundamental advance for conventional X-ray catheterization. It can enable new procedures not currently possible without surgery, such as non-surgical mitral neochordal implantation and direct mitral annuloplasty and can greatly simplify complex structural heart interventional procedures such as paravalvular leak repair, postinfarction and congenital muscular VSD repair, left atrial appendage closure, atrial and ventricular myocardial ablation procedures for rhythm disorders.

BRIEF DESCRIPTION OF THE DRAWINGS

This invention is described with particularity in the appended claims. The above and further aspects of this invention may be better understood by referring to the following description in conjunction with the accompanying drawings, in which like numerals indicate like structural elements and features in various figures. The drawings are not necessarily to scale, emphasis instead being placed upon illustrating the principles of the invention.

The drawing figures depict one or more implementations in accord with the present teachings, by way of example only, not by way of limitation. In the figures, like reference numerals refer to the same or similar elements.

FIG. 2 is a perspective view of several of the possible CMUT-on-CMOS array examples for 3D ICE;

FIGS. 19A-19C illustrate a transient simulation of analog OFDM with 2 7 MHz Gaussian pulses.

DETAILED DESCRIPTION OF THE INVENTION

Figure 1:
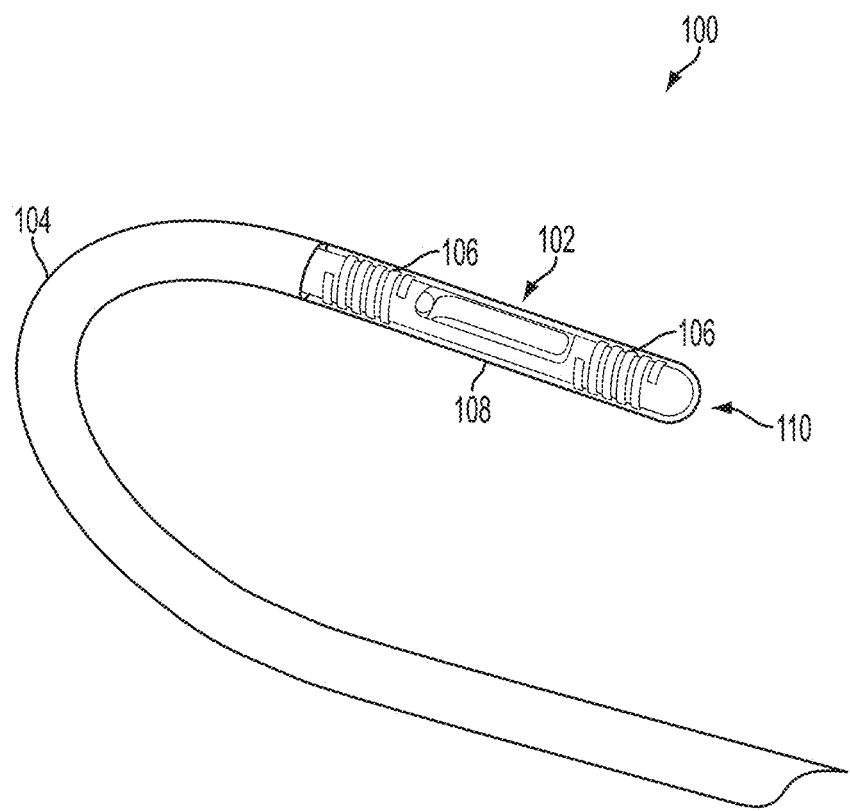
FIG. 1 is a distal-side perspective view of a three-dimensional MRICE catheter.

To facilitate an understanding of the principles and features of the various embodiments of the invention, various illustrative embodiments are explained below. Although exemplary embodiments of the invention are explained in detail, it is to be understood that other embodiments are contemplated. Accordingly, it is not intended that the invention is limited in its scope to the details of construction and arrangement of components set forth in the following description or illustrated in the drawings. The invention is capable of other embodiments and of being practiced or carried out in various ways. Also, in describing the exemplary embodiments, specific terminology will be resorted to for the sake of clarity.

It must also be noted that, as used in the specification and the appended claims, the singular forms "a," "an" and "the" include plural references unless the context clearly dictates otherwise. For example, reference to a component is intended also to include composition of a plurality of components. References to a composition containing "a" constituent is intended to include other constituents in addition to the one named.

Also, in describing the exemplary embodiments, terminology will be resorted to for the sake of clarity. It is intended that each term contemplates its broadest meaning as understood by those skilled in the art and includes all technical equivalents which operate in a similar manner to accomplish a similar purpose.

Ranges may be expressed herein as from "about" or "approximately" or "substantially" one particular value and/or to "about" or "approximately" or "substantially" another particular value. When such a range is expressed, other exemplary embodiments include from the one particular value and/or to the other particular value.

Similarly, as used herein, "substantially free" of something, or "substantially pure", and like characterizations, can include both being "at least substantially free" of something, or "at least substantially pure", and being "completely free" of something, or "completely pure".

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

It is also to be understood that the mention of one or more method steps does not preclude the presence of additional method steps or intervening method steps between those steps expressly identified. Similarly, it is also to be understood that the mention of one or more components in a composition does not preclude the presence of additional components than those expressly identified.

The materials described as making up the various elements of the invention are intended to be illustrative and not restrictive. Many suitable materials that would perform the same or a similar function as the materials described herein are intended to be embraced within the scope of the invention. Such other materials not described herein can include, but are not limited to, for example, materials that are developed after the time of the development of the invention.

FIG. 1 illustrates a full-volume 3D magnetic resonance intracardiac echography ("MRICE") catheter 100 with a tip including at least one CMUT-on-CMOS chip for Rx multiplexing and Tx beamforming 102. This example can take advantage of the CMUT-on-CMOS technology for 2D array design flexibility and on-chip transmit/receive beamforming electronics integration, recent advances in FPGA and graphical processing unit (GPU) based real-time ultrasound image processing, and MRI compatible catheter design and implementation. The 3D MRICE catheter 100 is MRI safe. The 3D MRICE catheter 100 can range in sizes from 6 French to about 10 French (French (Fr)=Diameter (mm)*3) and can have a 2-axis deflection point 104 to provide access and views for most intracardiac operations. Another element of the 3D MRICE catheter 100 is the inductively coupled coils 106, to provide visibility and to navigate the catheter tip 110 in space under MRI.

The 3D MRICE catheter 100 is similar in mechanical properties and steerability to current 2D ICE, and thus less likely to fail clinically. One example, as illustrated in FIG. 2, the CMUT-on-CMOS volumetric imaging array 102 can have a large area (7 mm×2.8 mm) to provide an array size with adequate spatial resolution, and large active area for acoustic power output for operation in 5-12 MHz range. This is also critical for electronics integration since spatially and temporally coded transmit signal generation and low noise received signal detection functionality can be contained in a single chip 102. One can also use a CMUT-on-CMOS in a multiple stacked chip configuration to have more area for electronics under the same array area as described in as described in U.S. Pat. No. 8,766,459, the disclosure of which is incorporated herein by reference.

As an example, the imaging can be done over a 90°×90° field of view ("FOV") at 5 cm and narrowing to 45°×45° at 15 cm. This is one example of a desired spatial range of most ASD, ventricular septal defect ("VSD"), left atrial appendage ("LAA") occlusion, and mitral procedures. Within this framework, 3D MRICE catheter 100 can provide: (1) Collection of full volumetric ultrasound image data over 5-15 cm penetration depth with less than 10 transmit firings; (2) high information rate over few transmission lines; (3) catheter and operational design to avoid MRI interference, and (4) thermal management of RF catheter heating.

To provide these benefits, the key features of the invention are:

1. CMUT-on-CMOS technology implementing large aperture 2D receive arrays with more than 100 elements and about 100 μm×100 μm element size for large FOV and integrated low noise electronics to obtain high SNR.

2. On-chip electronics that allow for massively parallel RF data transfer (in an example, greater than 200 MHz bandwidth per line) to capture volumetric image data in few transmit firings.

3. On-chip electronics and backend processing strategies for volumetric imaging with minimal motion artifacts, from simply defocused/focused, temporally coded defocused/focused to spatially coded multiplane phased array transmit beamforming implementation. This feature, along with massively parallel RF data transfer, can allow up to 50× reduction in cable count as compared to conventional cabling.

4. A 3D ICE catheter with as few as 14 transmission lines to minimize RF heating under MRI, and concurrent or (if necessary) coordinated MRI RF excitation to minimize MRI interference.

5. A closed-loop actively cooled MRI safe ICE catheter design using materials and techniques to minimize MRI artifacts and RF heating.

6. Inductively or conductively coupled marker coils for catheter tracking under MRI with minimized RF heating.

Sample array designs for 3D MRICE development are summarized in FIG. 2. In some examples, these are 2D CMUT-on-CMOS Arrays and On-chip Coded Beamforming that allow for 3D MRICE. These exemplary designs aim to obtain volumetric image data with minimum number of firings and achieve the required SNR for 5-15 cm imaging range. Initial designs can have 90°×90° FOV at approximately 5 cm and 45°×45° FOV at approximately 15 cm, selectable electronically. To maximize the active area, in all array designs, the full silicon surface is covered by CMUT elements overlaying the CMOS electronics. In this example, the 192 element receiving ("Rx") arrays 200 are placed at the periphery to maximize the Rx aperture. In some other embodiments the Rx array can have cross or plus shapes to cover the entire aperture with smaller number of elements. In general, well-known 2D sparse array designs can be utilized to form the Rx arrays. Also, all of the Rx elements 200 read out in parallel during one or two Tx firings, as described later. The example of ICE1 facilitates Rx electronics and real-time imaging system. A transmitting ("Tx") array 202 can be kept simple in ICE1 204. The Tx array 202 can be driven by a short pulse or coded excitation to further improve SNR. In an example, a 14 dB gain in SNR with 13 bit, 2 cycle, 2.5 µs codes can be achieved with dual-ring CMUT-on-CMOS arrays. The Tx array 202 fires a defocused imaging pulse received by the Rx arrays 200.

Another example ICE2 206 design improves the lateral resolution beyond current 2D ICE arrays by Tx beamforming in both directions and operating at 10 MHz center frequency. It can also achieve ~2 mm slice thickness in elevation at 5 cm. Another example ICE3 208 design can add phased array capability with spatial and temporal coding. In this example, an image over a 2D plane can be obtained during each Tx firing. Up to 90 plane images, which can be displayed in multiplanar format, can be collected to form the 3D volume. In this case the volumetric image is formed plane by plane where image for each plane is collected using one or two transmit firings. Improved resolution in ICE2 206 and ICE3 208 can be realized using improved SNR from design improvements, coding, and increasing the imaging frequency. In this example, these approaches enable full volumetric imaging with minimum motion artifacts. Although Doppler flow is not considered, flow measurement over 2D planes can be implemented as part of the real time imaging system using correlation techniques over frames obtained during consecutive firings.

In other examples of the invention, the on-chip electronics with massive RF multiplexing for fast full volume imaging overcomes one of the challenges for on-chip electronics. The examples of the invention can overcome the difficulty of the parallel readout of 192 Rx channels over 8 RF transmission lines during each firing. Overcoming this existing limitation can reduce the total number of transmission lines. This can be achieved by FDM or TDM using interleaved samples from different Rx channels on the same line. This same technique can be used to reduce the number of cables for 1D ICE arrays for other purposes including making them suitable for use under MRI.

Figure 3:
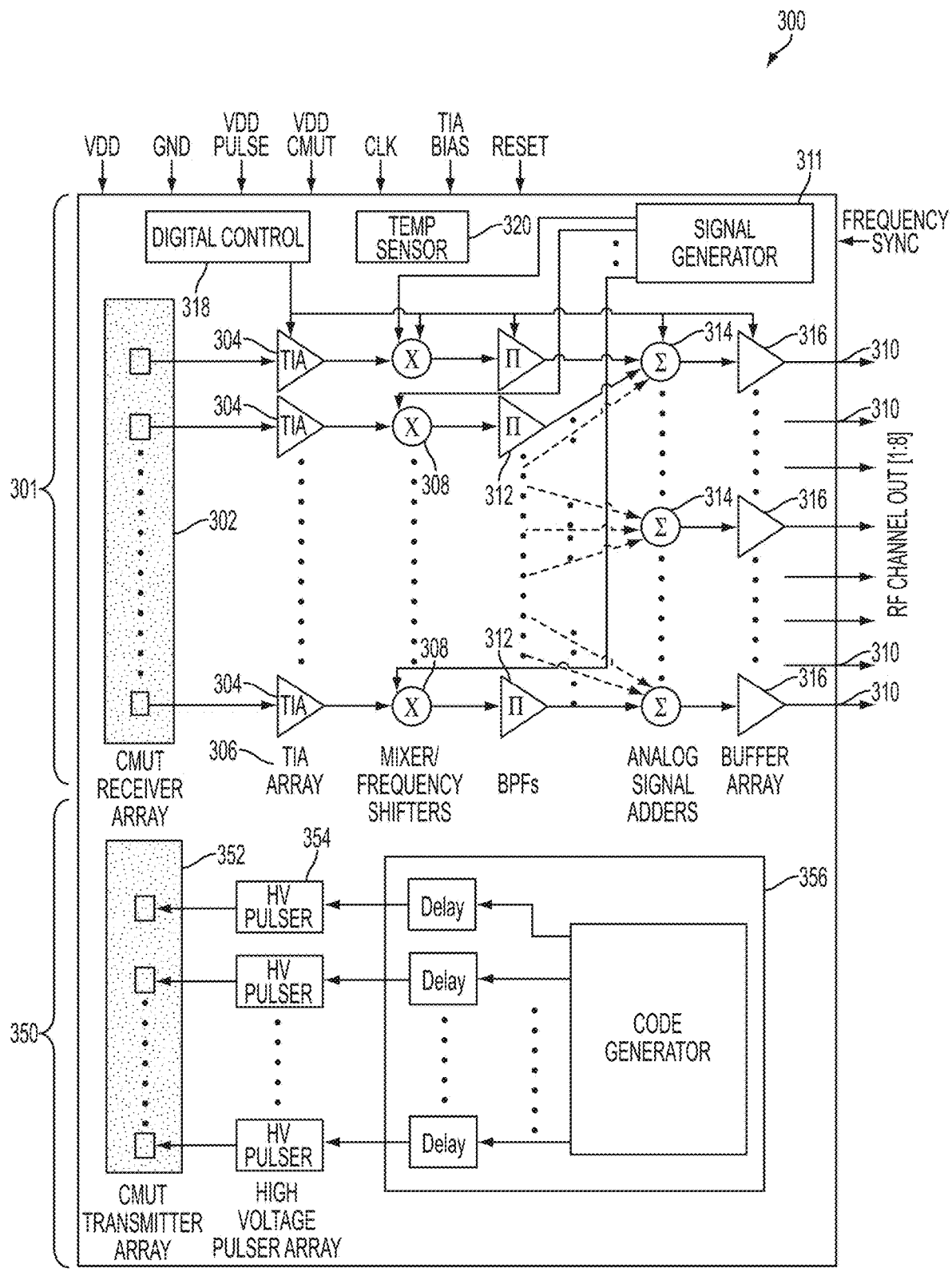
FIG. 3 is an example high level circuit schematic of the on-chip electronics for massively parallel Rx RF data transfer and on-chip Tx beamforming.

A multiplexing component 301 is illustrated by example using a FDM solution can be analog Quadrature Amplitude Modulation ("QAM"), which is a form of FDM. An example of a FDM solution using QAM 300 is illustrated in the overall electronics schematic of FIG. 3. At the output of each Rx element 302 there can be a metal oxide semiconductor ("MOS") feedback TIA 304. The MOS feedback TIA 304 can provide low noise, high bandwidth and adjustable gain. The gain of the TIAs 304 can be dynamically changed for time gain compensation. The power consumption of each TIA in this example can be about 0.825 mW and the entire TIA array 306 consumes 132 mW. Signals from the TIAs 304 can be fed to single balanced MOS Gilbert mixer 308 to shift their frequencies to implement the analog QAM. This example can shift the TIA outputs so that with each carrier frequency and its quadrature component can shift two TIA outputs. Thus, using 12 high frequency carriers (e.g., 40, 80, 100, 120, 140, 160, 180, 200, 220, 240, 260 and 280 MHz) and their quadrature component, 24 TIA outputs can be shifted and sent out via single cable 310. These RF cables 310 can be chosen to have sufficient bandwidth and minimized electrical crosstalk. To avoid interference from MRI signals, the frequencies around the MRI Larmor frequency (around 63.9 MHz for a 1.5 T system) may be avoided. The carrier signal can be generated by an on chip arbitrary waveform generator 311 or by frequency multipliers using an external clock. After the mixer 308, each signal can be passed through a bandpass filter ("BPF") 312 to suppress the side band and harmonics. The mixers 308 and BPF bank 312 consumes approximately 120 mW and 225 mW power, respectively, in this example. After the BPF stage 312, signals can be added using analog adders 314 and sent off chip through analog buffers 316. The analog buffers 316 can consume about 70 mW power, for example. A digital control circuit 318 can be used to power down of the receiver circuits while the catheter is not collecting data. Therefore, in this example, the chip 300 can consume about 0.6 W peak power on the receiver side.

The average power can be much lower since even in the ICE2 206 design, the chip can be active for only 18 ms of a 50 ms duty cycle at 20 frames/second. Even when the average power consumption of the Tx side is added, the overall figure can be significantly lower than 3-4 W consumed in 2D ICE catheters, again due to lower duty cycle. An on-chip temperature 320 sensor can be implemented for continuous monitoring of MRI induced heating, and the chip can have a shut off feature when the temperature exceeds 43° C.

On the transmit side, a beamforming component 350 can be used and is illustrated in an example having each CMUT transmitter element 352 connected with a high voltage on chip pulser 354. To change the FOV depth from 5 cm to 15 cm, the pulse repetition rate can be changed. In one example, this can be done by using an on-chip counter 354. A temporal and spatial coded excitation sequence can be used in the ICE chips 300, the code can be stored on-chip using a flash memory array, floating gate arrays or can be generated using digital logic circuits and a clock signal. For programming the on-chip flash memory, a few extra cables can be required which can be cut off once the chip is programmed before mounting on the catheter 100.

In an example of ICE1 204, DC voltages can be applied directly, or DC voltages can be generated on chip from an AC input signal to improve electrical safety and to further reduce the transmission line count to 14. This represents 15×, 25× and 50× reduction in transmission line number as compared to traditional implementations of the ICE1, ICE2, and ICE3 arrays 204, 206, 208, respectively, considering that ICE3 308 array has 704 elements.

Figure 4A:
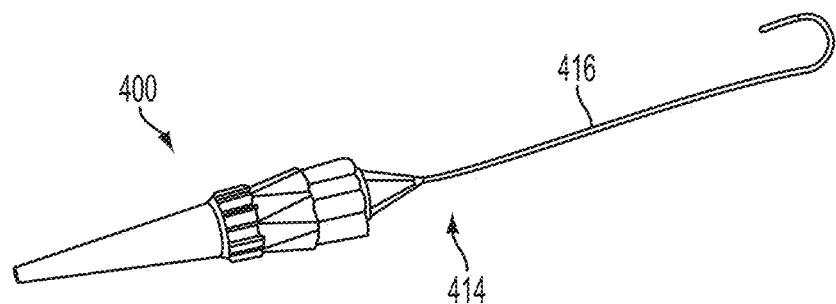
FIGS. 4A and 4B are the handle and a cross-section of the proximal end, respectively, of an example of a three-dimensional MRICE catheter.
Figure 4B:
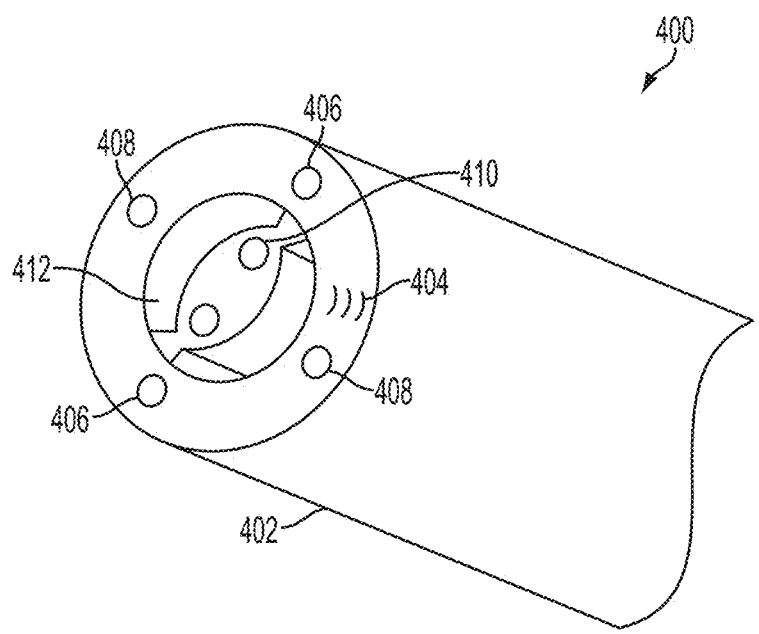

FIGS. 4A and 4B illustrate an example of a 3D ICE catheter design for MRI safe operation. The sterile, single-use 3D MRICE catheter 400 shown in FIGS. 4A and 4B can have a working length of approximately 110 cm. In an example, a 10 Fr catheter shaft 402 can have several biocompatible polymer layers 404 with different durometers. The metal content (i.e. pulling wires for tip deflection and braiding) can be minimized to reduce the RF induced heating risk during MRI, and to reduce artifact susceptibility which may obscure nearby anatomy.

In an example, the proximal shaft 402 can be reinforced with non-metallic fibers (e.g., Vectran® or Kevlar®) instead of Nitinol or MP35N alloy braiding wires. The non-metallic fibers can preserve catheter pushability and torquability. The catheter 300 can have a cylindrical enclosure 108 to house the side looking CMUT-on-CMOS chip 102, 204, 206, 208, and a round atraumatic distal tip 110. A semi-rigid polymer or MRI compatible metals can be used in the enclosure body depending on the final design.

In a manufacturing example, the enclosure 108 can be designed using 3D CAD software (e.g., Wildfire 4.0, Pro-Engineer). A metal model from the CADs can be manufactured from thin wall nitinol tube using 4-axis laser metal processing equipment (e.g., ProLas, Lasag Laser Industries)

and the polymer model can be formed using a rapid prototyping system (Uprint, Strasys Inc., MN).

Non-planar inductively coupled marker coils or loop coils 106 (that can provide separate receive channels connected to a scanner via coaxial transmission lines) can be embedded into both ends of the enclosure groove 108, in order to impart unambiguous real-time MRI visibility and trackability to the catheter 100. While the SNR of inductively coupled coils can be orientation dependent, this example allows further miniaturization by eliminating coaxial transmission lines, which occupy valuable space within the catheter shaft and which also would contribute to RF induced heating.

The example of the multi-lumen thermoplastic catheter shaft 402 shown in FIG. 4B can have lumen space for pulling wires for two-plane deflections. One set of wires can pass through anterior and posterior cable lumens 406 and left-right cable lumens 408. The shaft can further have lumens 410 for an ultrasound system cable, and open and closed loop saline cooling lumens 412. A polytetrafluoroethylene (PTFE) liner can be used in the pull cable lumens 406, 408 to reduce friction during use. Different durometers of otherwise matching design can be used in different sections of the catheter to accommodate deflection. A non-metallic braiding can be performed over the first shaft layer using a vertical 16-head braiding machine (e.g., a K16 Vertical braider, Steeger). The braiding angle can change between 20° and 60° (which affects the torquability) and braiding density can change between 35 and 80 picks per inch (which affects the shaft stiffness and pushability) can be optimized in non-metallic fibers to resemble metallic braided shaft mechanical properties. The final PEBAX (polyether block amide) layer can be applied using reflowing technique (e.g., 810 Shrink cycler, Beahm Designs) to create a smooth catheter surface.

A distal tip deflector mechanism 414 (see FIG. 4A) for two different planes can be designed and manufactured from vertebrated nitinol super elastic alloy. The deflection can occur for the distal 70 mm to achieve the desired 30-35 mm radius of curvature. The deflection angle can be up to 180° in each direction. The non-metallic sets of pull-cables can be fixed on the metal deflection mechanism and each of the pulling wire can be advanced into the dedicated lumen 406, 408 within the catheter shaft. The CMUT-on-CMOS imaging chip 102 can be connected to the signal carrying cables directly via wire bonding or soldering technique. The cables can be bundled to reduce the occupied volume and can be advanced into the catheter shaft using dedicated micro lumens. The cables can be soldered to the custom design male connector at the proximal end of the catheter. There can be two dedicated lumens 410 for the ultrasonic imaging array cables. The cable lumens 410 can be surrounded by cooling lumens 412 which can be used for closed-loop circulating-liquid cooling. In some cases, an open loop cooling system where the cooling fluid is disposed into the blood stream can be used.

The system can handle any RF induced heating of the transmission lines when under MRI. Although the CMUT-on-CMOS silicon chip 102 is not expected to heat under MRI, the cooling can also remove the heat conducted to the chip through the solder connections. The two separate lumens 412 can converge at the distal end and can connect to a rotary circulation pump. The liquid circulation speed can be adjusted based on the real time temperature measurement through embedded thermistor probe located on the CMUT-on-CMOS chip 102, 204, 206, 208 in the 3D MRICE catheter 300. The temperature data can be transmitted on one of the RF output cables when no imaging data is being collected and before the power is turned off for the next frame. The 3D MRICE system can provide that data to the display located in the MR control room and also to the cooling system controller that adjusts the rotary circulation pump speed within predetermined range. Both the controller and the rotary circulation pump can be located in the MRI control room. The temperature data can be projected to the MRI room for the operator's review. The 3D MRICE catheter handle 416 can provide dedicated buttons to control deflection amount and direction for each plane with single-handed operation. The proximal end of the handle also has dedicated ports to be connected to the imaging equipment and the cooling pump.

Figure 5:
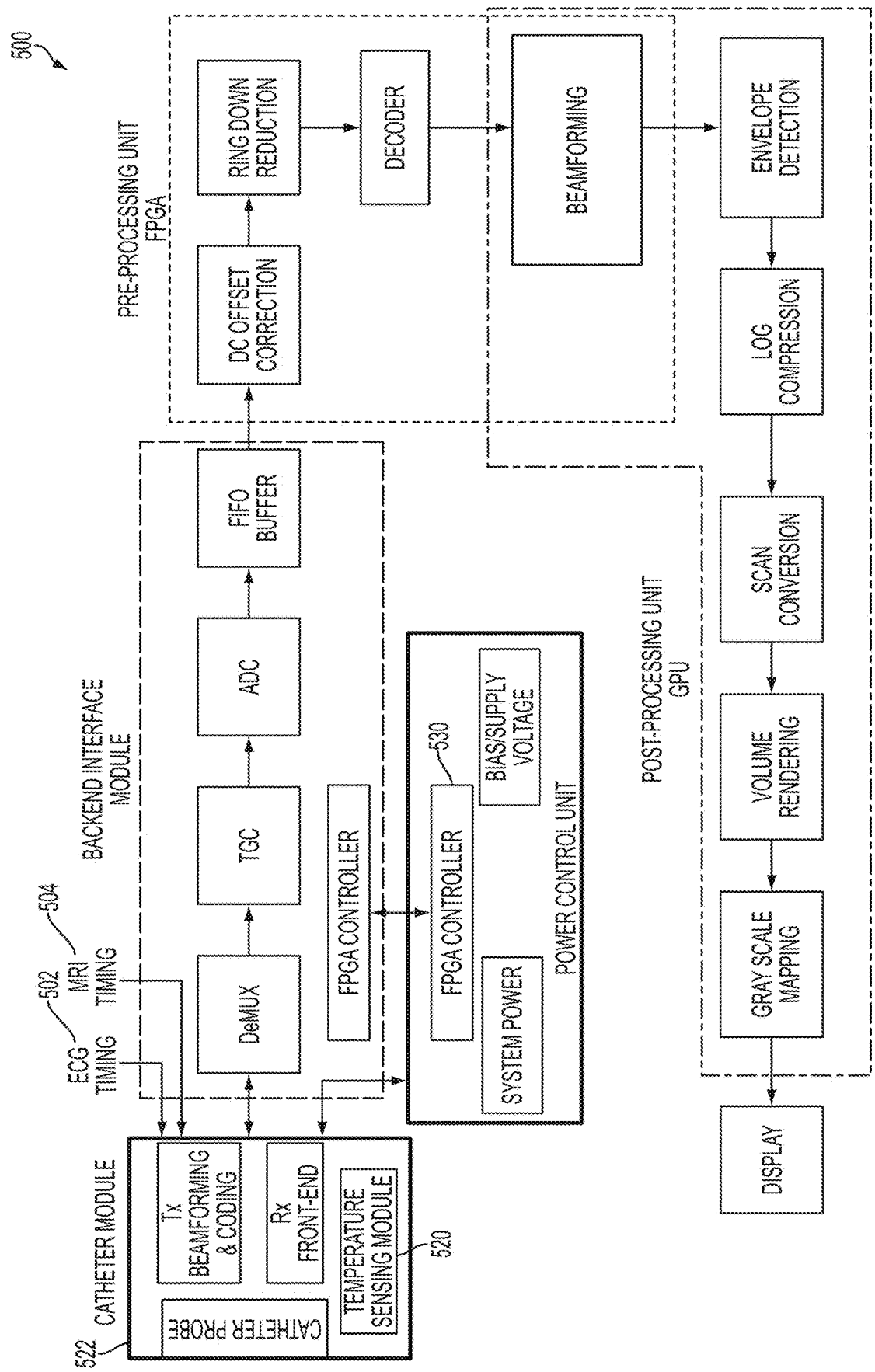
FIG. 5 is a block diagram of an example of a real-time imaging system.

The imaging system can include a graphics processing unit ("GPU") based real-time 3D MRICE volumetric imaging and graphical user interface ("GUI") for flexibility in implementing different beamforming schemes and image processing, as illustrated in FIG. 5. The system 500 can have an Electrocardiography ("ECG") input 502 for synchronization and display. The system 500 can also be synchronized with an MRI system for simultaneous operation or, time multiplexed (interleaved) operation, if needed. Timing information can be transferred to the imaging chip through the clock and reset inputs 504. The temperature sensor 520 on the CMUT-on-CMOS chip 522 can be readout over the RF lines once per frame with proper timing in order not to interfere with the RF ultrasound signals.

The other relevant system and processing requirements of the ICE arrays 204, 206, 208 are given in FIG. 2. A part of the system 500 can be implemented through minor modifications to many generic ultrasound imaging platforms available from commercial vendors like Verasonics or some research platforms such as Ultrasound Array Research Platform ("UARP") system developed in University of Leeds. The approaches to implement the system 500 would use combinations of a field programmable gate array ("FPGA") and a GPU to perform the digital computations efficiently. The volumetric image rendering can be performed on a GPU using application specific software which can utilize public resources such as the Gadgetron Open Source software.

For real time volume rendering and multi-plane image reconstruction, an Open Source framework for medical image reconstruction, the Gadgetron, which has recently been developed at the NHLBI and at Aarhus University, Denmark, can be utilized. Several previous projects have already demonstrated that it is indeed possible to obtain the desired volumetric rendering rates on the GPU, and that high performance open source software tools are available, as well as several tutorials from leading graphics conferences. The GUI for this application can resemble commercial 3D TEE and can depict multiplanar 2D images and surface-rendered 3D volumes. It also can allow 3D point-marker placement for complex geometry assessment.

Figure 6:
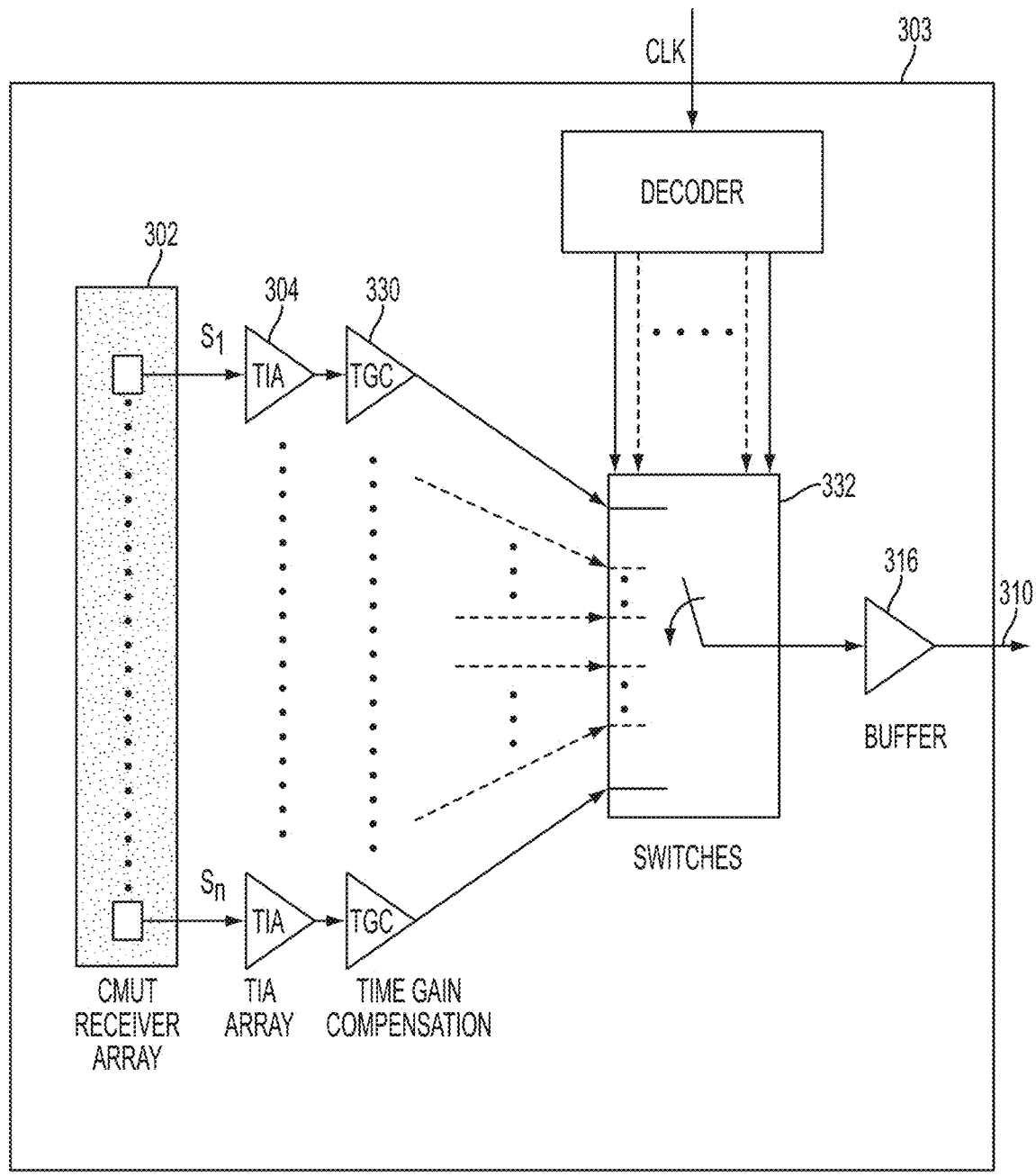
FIG. 6 is an example high level circuit schematic of a portion of the on-chip electronics for another example for massively parallel RF data transfer.
Figure 7:
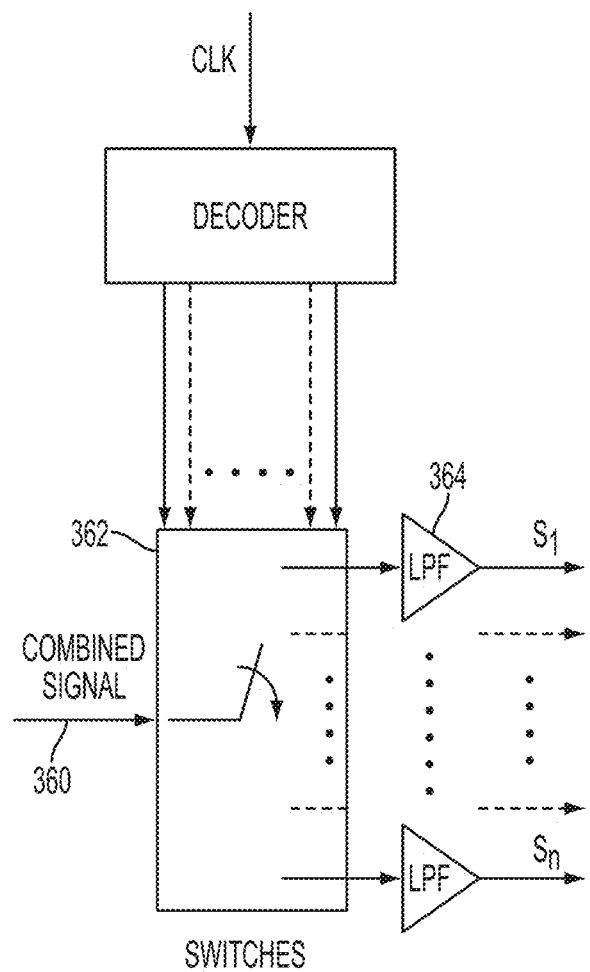
FIG. 7 is an example high level circuit schematic of a portion of the on-chip electronics for demodulating the combined signal of FIG. 6.

In a further example of the multiplexing component, the reduction of cables of ICE can also be achieved by implementing on-chip high frequency TDM. FIG. 6 illustrates TDM multiplexing component 303 for this example. Here, the TIA 304 amplifies the CMUT current signals as before. However, the TIA's 304 output now can be dynamically changed with a TGC circuit 330 to account for time gain. Each of TGC's 330 output is sampled at more than the Nyquist rate (which is twice the bandwidth of the bandlimited channel) in a synchronized way with a TDM switch 332. Further, the output can be sent via single path and the signal is sent out via output buffer 316. FIG. 7 illustrates one example of how a combined signal 360 can be recovered.

The combined signal 360 can sent to a de-multiplexer (switch) 362 and then transmitted through a low pass filter 364.

In an example of ICE1 204, DC voltages can be applied directly, or DC voltages can be generated on chip from an AC input signal to improve electrical safety and to further reduce the transmission line count to 14. This represents 15×, 25× and 50× reduction in transmission line number as compared to traditional implementations of the ICE1, ICE2, and ICE3 arrays 204, 206, 208, respectively, considering that ICE3 308 array has 704 elements.

FIGS. 8-21 illustrate an example of a multiplexing component 800 using orthogonal frequency division modulation or multiplexing ("OFDM"), and specifically analogue OFDM. In this method, in the multiplexing step, the message signals from consequent channels are mixed with sine and cosine signals at a carrier frequency and added, with the final signal expressed as:

$$X(\omega) = \sum_{n=0,1,\ldots k} m_{2n+1}(\omega) * \cos(\omega_n) + m_{2n+2} * \sin(\omega_n)$$

For demodulation, the received signal is mixed with orthogonal sine and cosine signals at the modulation frequency and then low pass filtered to get back the message signals as:

$$X(\omega) * \cos(\omega_n) \xrightarrow{LPF} m_{2n+1}$$
$$X(\omega) * \sin(\omega_n) \xrightarrow{LPF} m_{2n+2}$$

Figure 8:
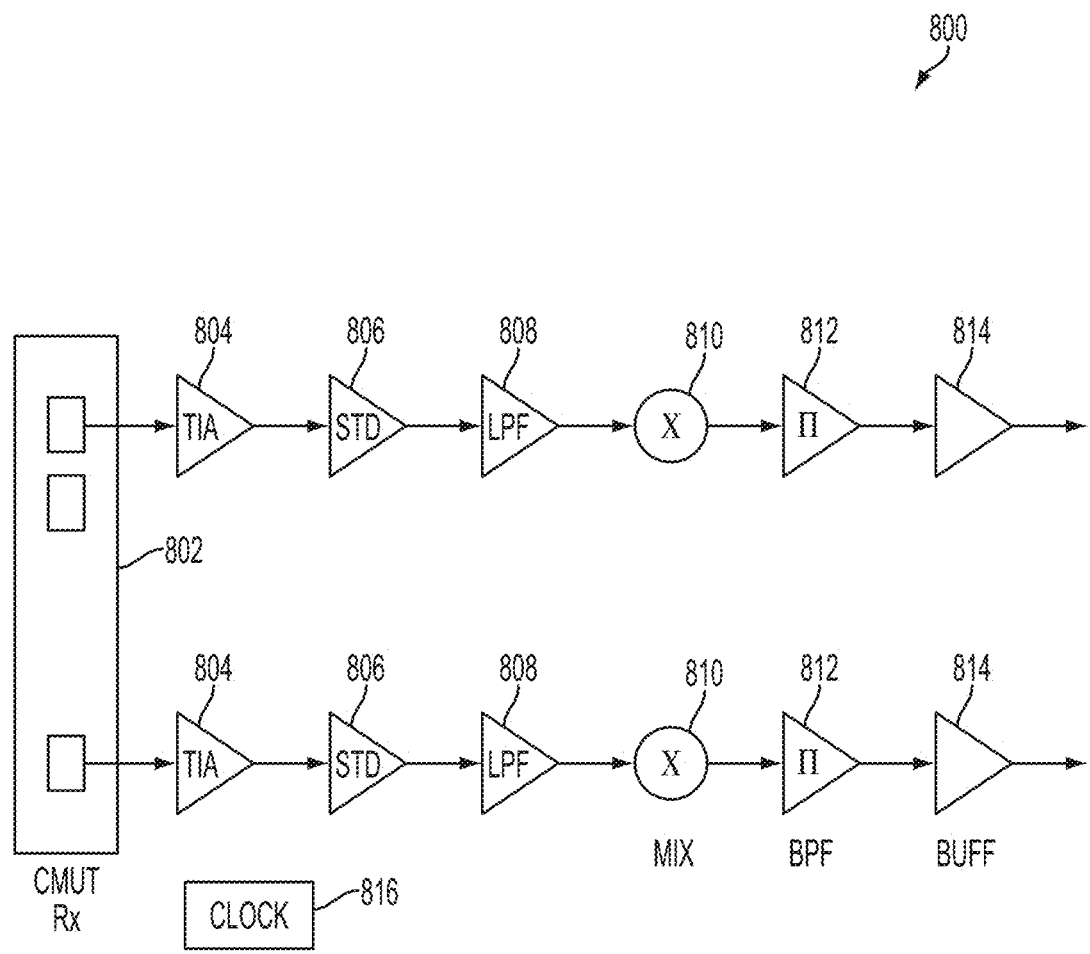
FIG. 8 is a further example high level circuit schematic of the on-chip electronics for massively parallel Rx RF data transfer.
Figure 9:
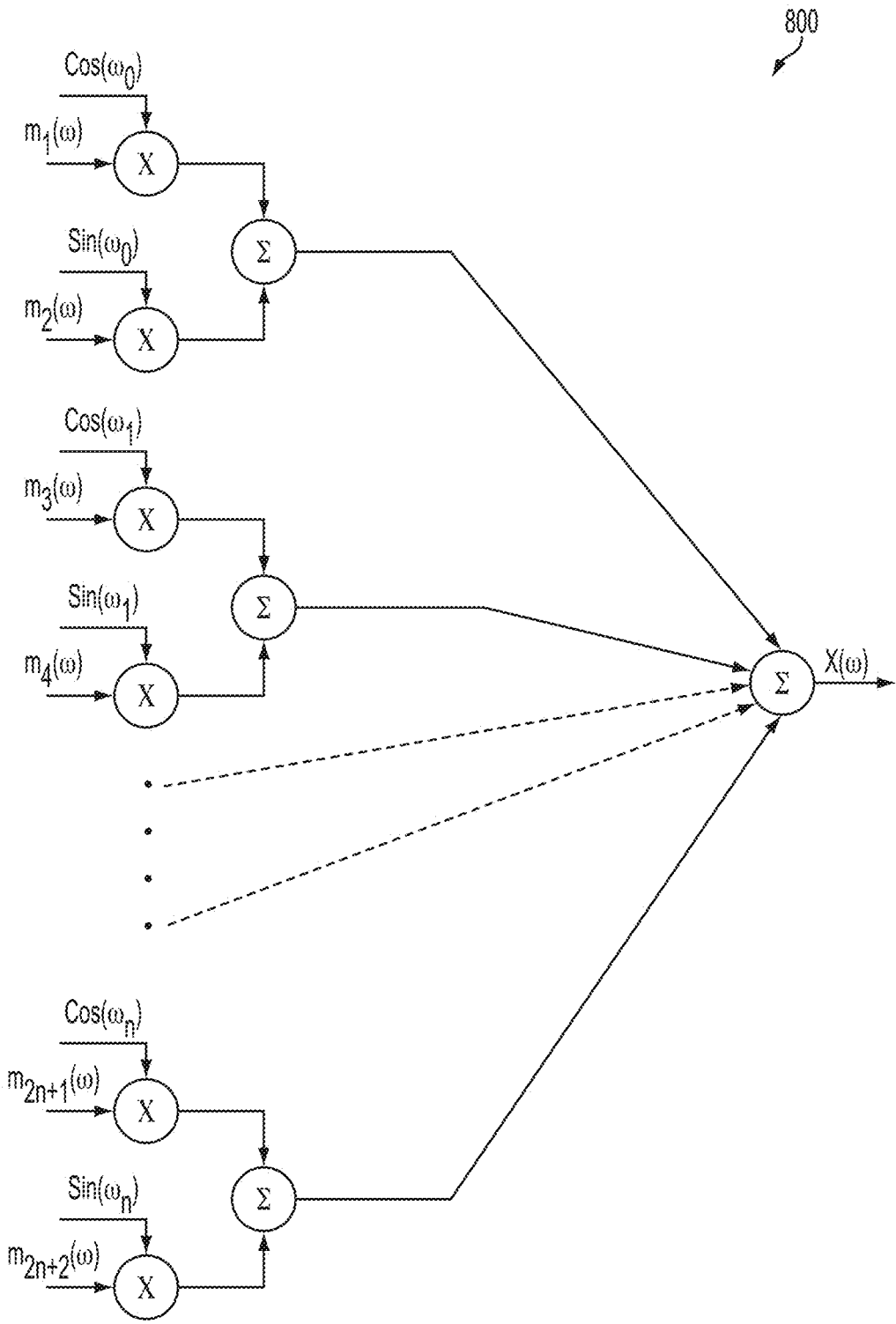
FIG. 9 illustrates a bock diagram of an example of analog OFDM.
Figure 10:
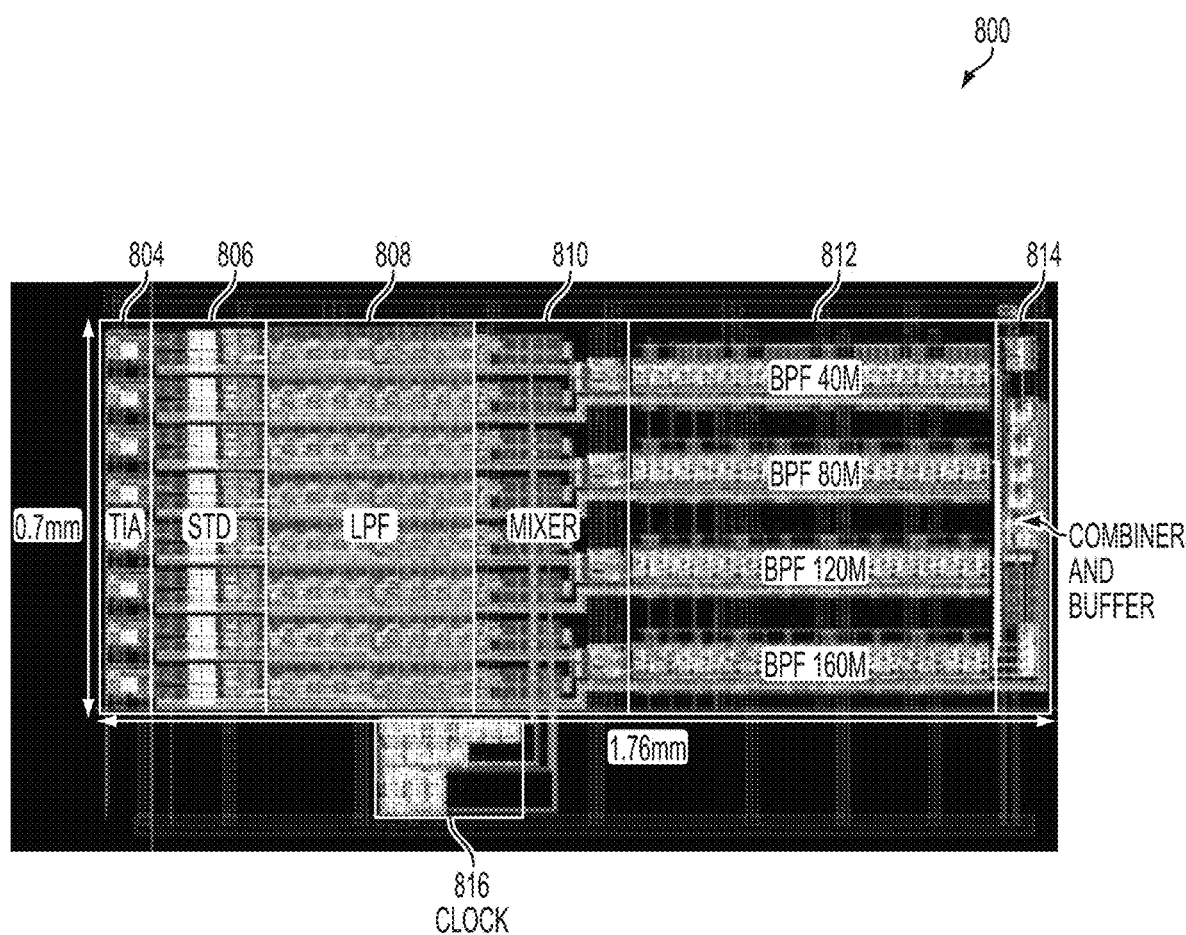
FIG. 10 illustrates a layout of an example of an 8 channel OFDM circuit for ICE.

FIGS. 8, 9 and 10 illustrate different descriptions of the OFDM multiplexing component 800. FIG. 10 illustrates an integrated circuit custom designed to multiplex the output of 8 CMUT array elements with center frequency 7 MHz and 80% fractional bandwidth for ICE application. Parallel readout of 8 CMUT signals over single RF transmission line during each firing was achieved by implementing on chip analog OFDM with modulation frequencies of 40 MHz, 80 MHz, 120 MHz and 160 MHz. These frequencies are chosen to provide enough separation between channels as well as avoiding the 64 MHz MRI signal in a 1.5 T system, as noted above. The IC was designed in 0.35 μm 4M2P TSMC process with supply voltage of 3.3V and the layout of the circuit consumes 0.7×1.76 mm² area.

FIGS. 8 and 10 illustrate the sequence of components. The Rx elements 802 transmit their output to a capacitive-feedback TIA 804 and the single ended signal of the TIA 804 can be converted to fully differential with a STD 806. A low pass filter ("LPF") 808 filters the signal outputted from the TIA 804 and the STD 806 and sends it to a passive mixer 810 to modulate the signal to an orthogonal carrier frequency. To eliminate the harmonic generated by the passive mixer 810, the signal is then put through a BPF 812 and then on to a buffer 814 before transmitting the output signal off the chip 800.

Figure 11:
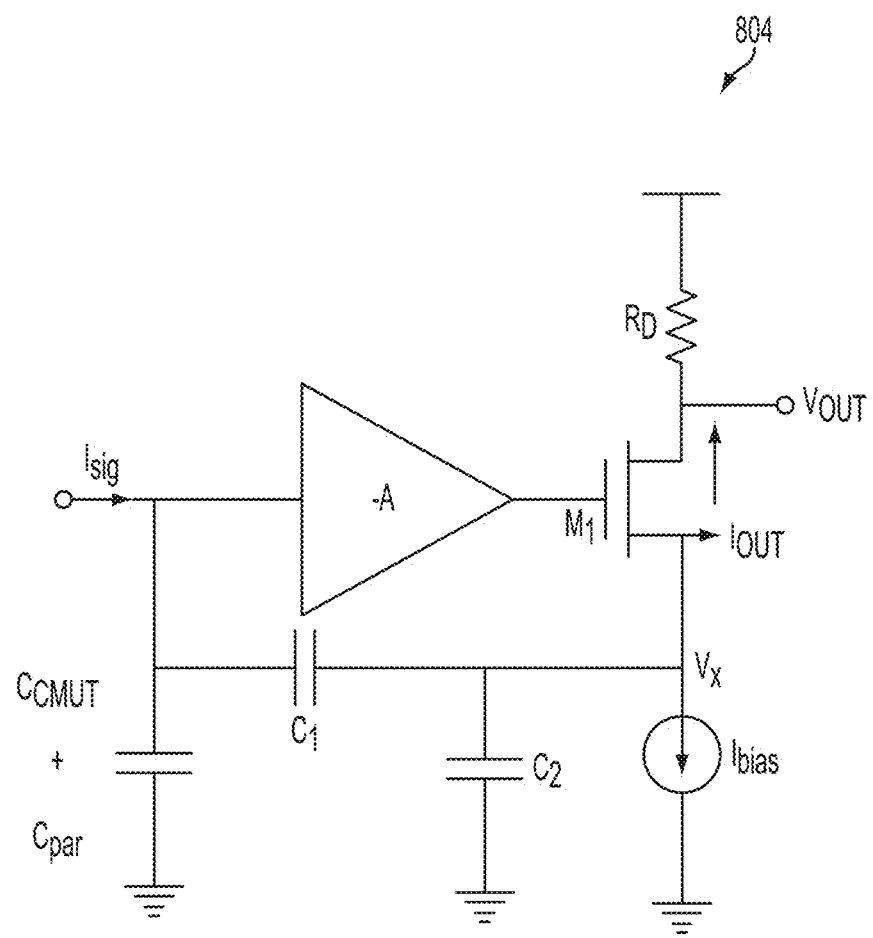
FIG. 11 is a schematic of a capacitive feedback TIA.

Specifics regarding some of the components of the OFDM multiplexing component 800 are illustrated in FIGS. 11-14 and discussed below. FIG. 11 illustrates the capacitive-Feedback TIA 804. It can be the first component of the receiver chain acting as a low-noise preamplifier. Common to all sensor front-end circuits, the first amplifier's noise performance in the receiver path determines the SNR of the entire signal path. For its low input referred noise, high gain and high bandwidth feature the capacitive feedback TIA 804 can be used to amplify the CMUT's output current. In this example, the TIA's 804 simulated bandwidth can be ~20 MHz and Gain 89 dBΩ and noise 16 pA/√Hz. The power consumption of each TIA 804 can be approximately 0.551 mW.

Figure 12:
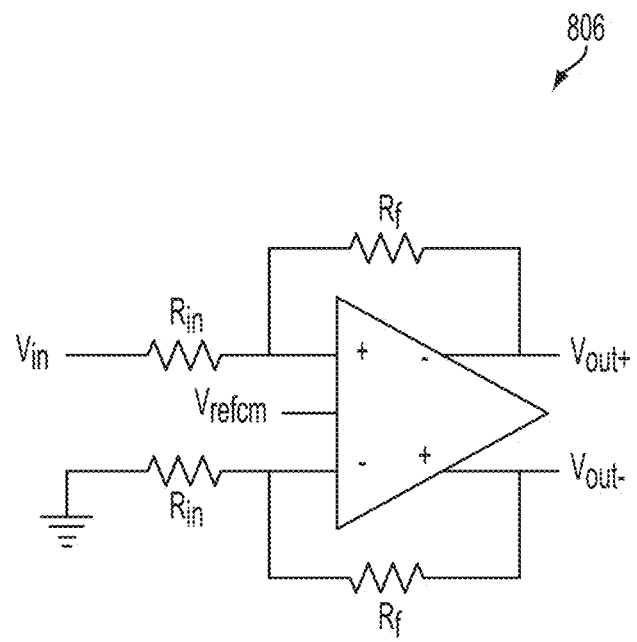
FIG. 12 is a schematic of the STD.
Figure 13:
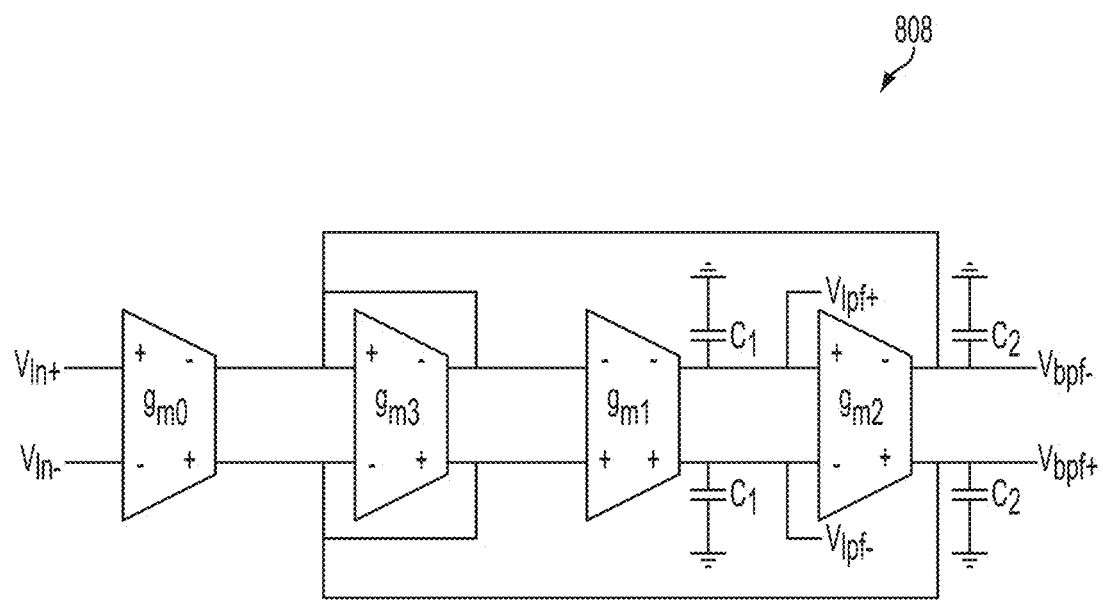
FIG. 13 is a schematic of an example of a biquad structure used for designing gm-C low pass and band-pass filters.

The STD 806 can convert the single ended signal of the TIA 804 to a fully differential signal. Fully differential signal processing reduces the effect of external noises, clock injection and even order harmonic and increases dynamic range. FIG. 12 illustrates the STD circuit schematic. FIG. 13 illustrates an example of the anti-aliasing LPF 808. In this example, a fully differential 4th order biquad tunable gm-C low pass filter is used to limit the filter is designed to band limit the TIA's 804 output signal. Each LPF 808 can have a −3 dB bandwidth of 11 MHz and consume 6.7 mW power. FIG. 13 shows the biquad structure of the gm-C filter. Other examples can eliminate the LPF 308 by adjusting the CMUT array element frequency response.

Figure 14:
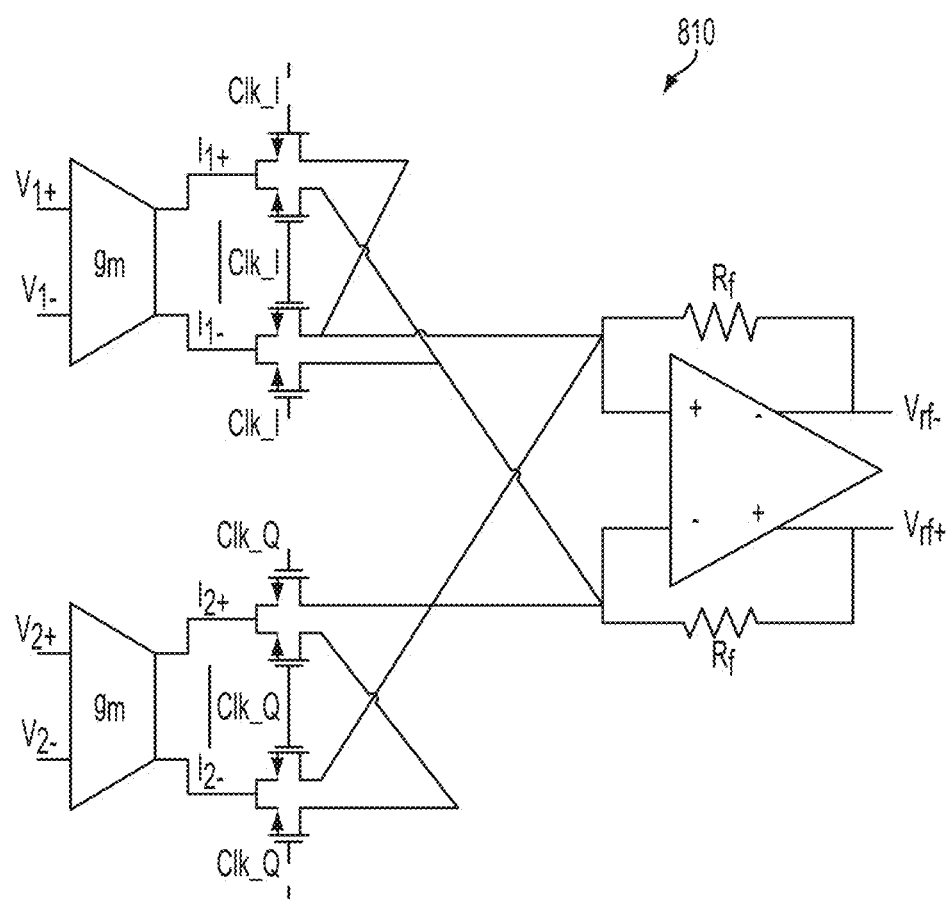
FIG. 14 is a schematic of an I/Q passive mixer.

The passive mixer 810 can be designed to modulate the outputs of multiple (in this example 8) different LPFs 808 with orthogonal carrier frequency of 40 MHz, 80 MHz, 120 MHz and 160 MHz. FIG. 14 shows an example of an I/Q passive mixer 810 structure. The BPF 812 can be utilized to eliminate the harmonic generated by the passive mixer 810. In an example, four 8th order tunable gm-C biquad bandpass filters 812 with center frequency 40 MHz, 80 MHz, 120 MHz and 160 MHz can be used. The bandwidth of each BPF 812 can be ~30 MHz. The power consumption of each BPF 812 can be 23 mW. The outputs of the BPFs 812 can be combined using a power spectrum combiner circuit known in the art. An instrumentation amplifier can also be used to convert the differential output of combiner circuit to single ended.

The buffer 814 can be a current feedback source degenerated push-pull type. A simulated bandwidth of the buffer 814 can be ~350 MHz for a load of 35 pf∥1MΩ. Further, a clock generator 816 can be provided. In an example, two clocks of 240 MHz and 320 MHz are supplied externally. Using divide by 3, and a walk-in-ring oscillator circuit, the 40 MHz orthogonal carrier signals are generated from 240 MHz signals. Using divide by 2, and a walk-in-ring oscillator circuit, the 80 MHz orthogonal carrier signals can be generated from 320 MHz. 120 MHz and 160 MHz orthogonal carriers can be generated by feeding 240 MHz and 320 MHz clocks directly to walk-in-ring oscillator respectively.

Figure 15:
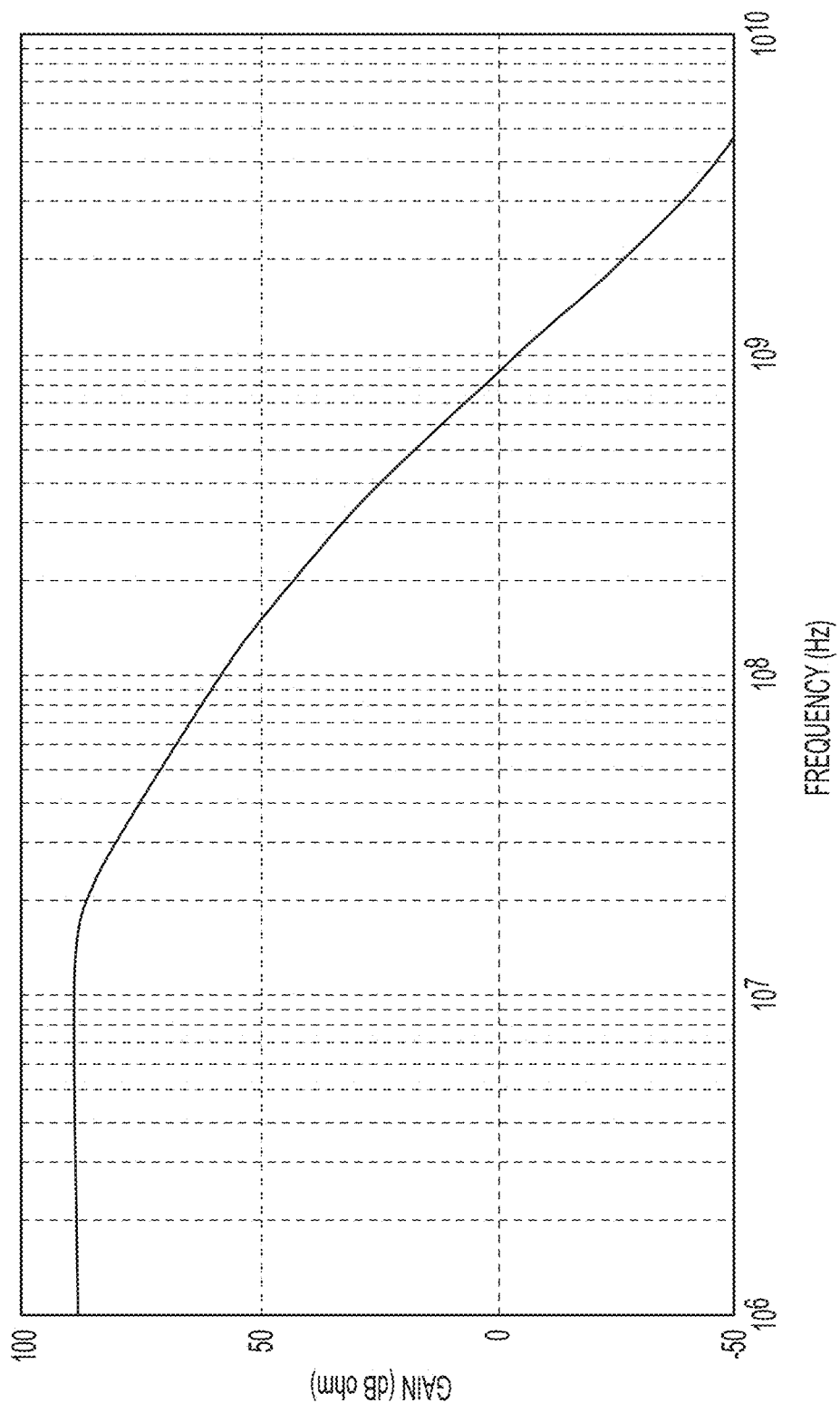
FIG. 15 illustrates a simulated frequency response of the capacitive feedback TIA.
Figure 16A:
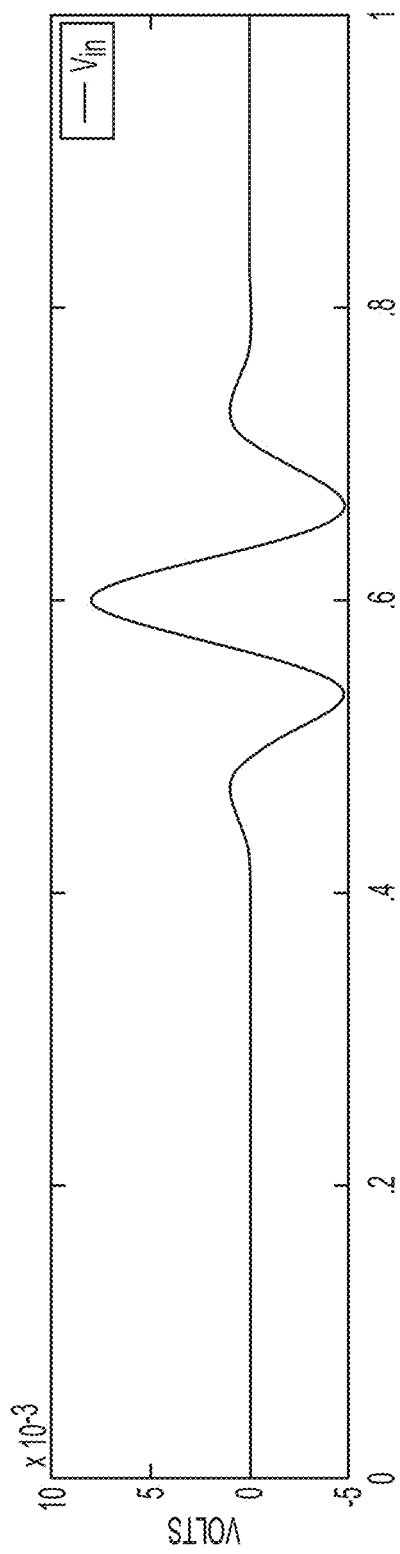
FIGS. 16A and 16B illustrate the transient simulation results of the single to fully differential conversion circuit.
Figure 16B:
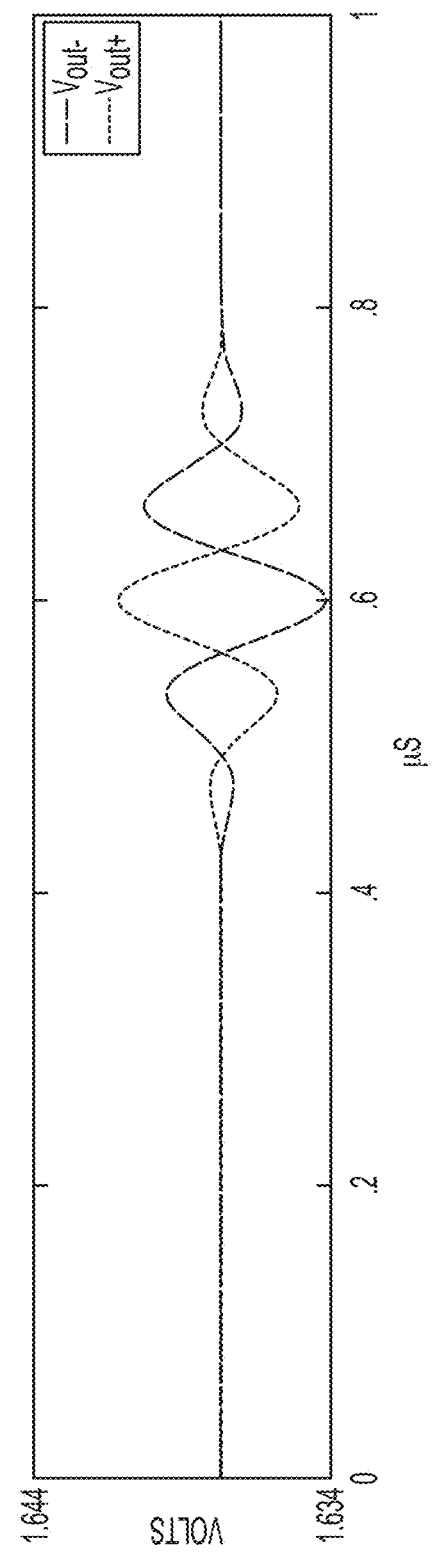
Figure 17:
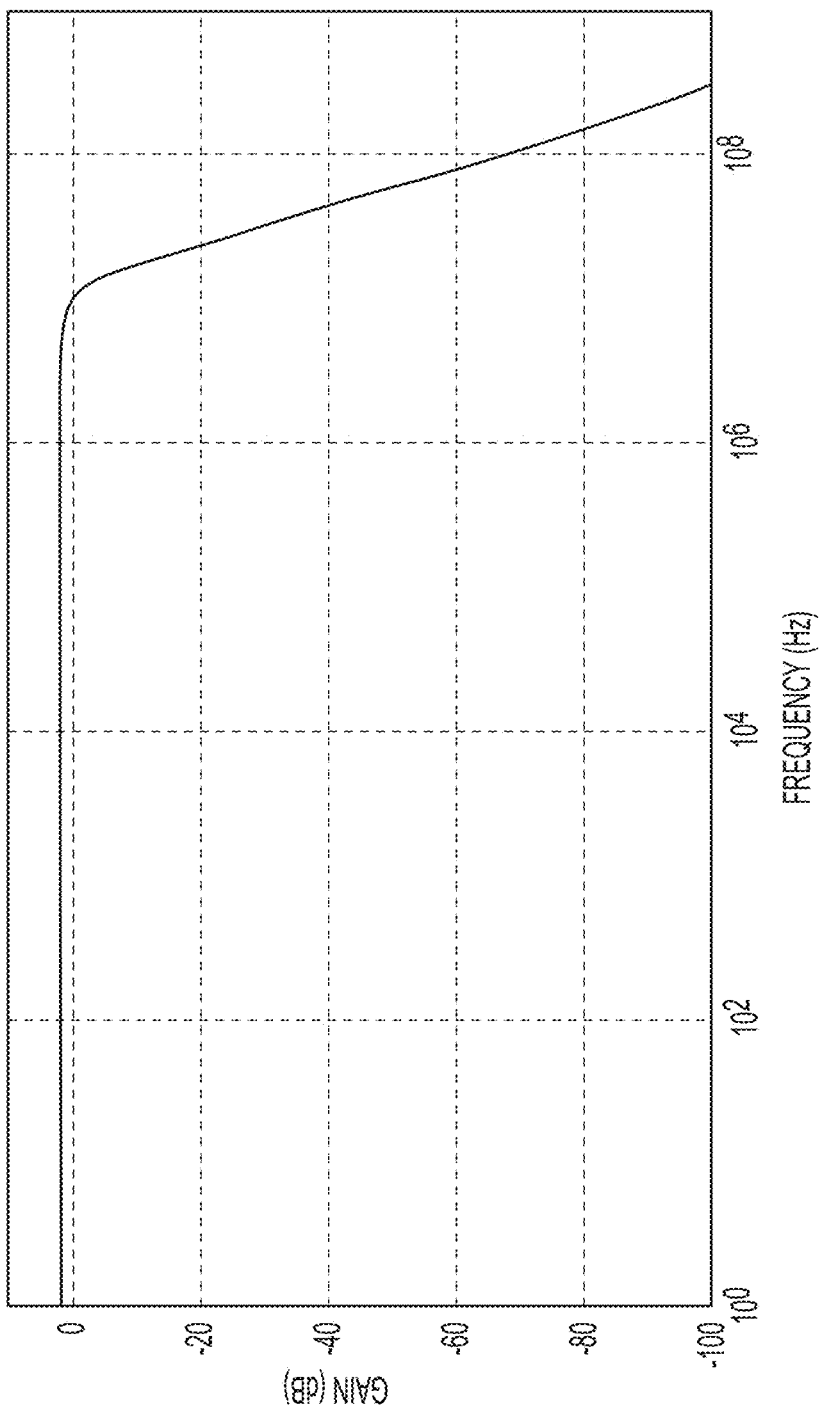
FIG. 17 illustrates a simulated Frequency response of 4th Order LPF.
Figure 18:
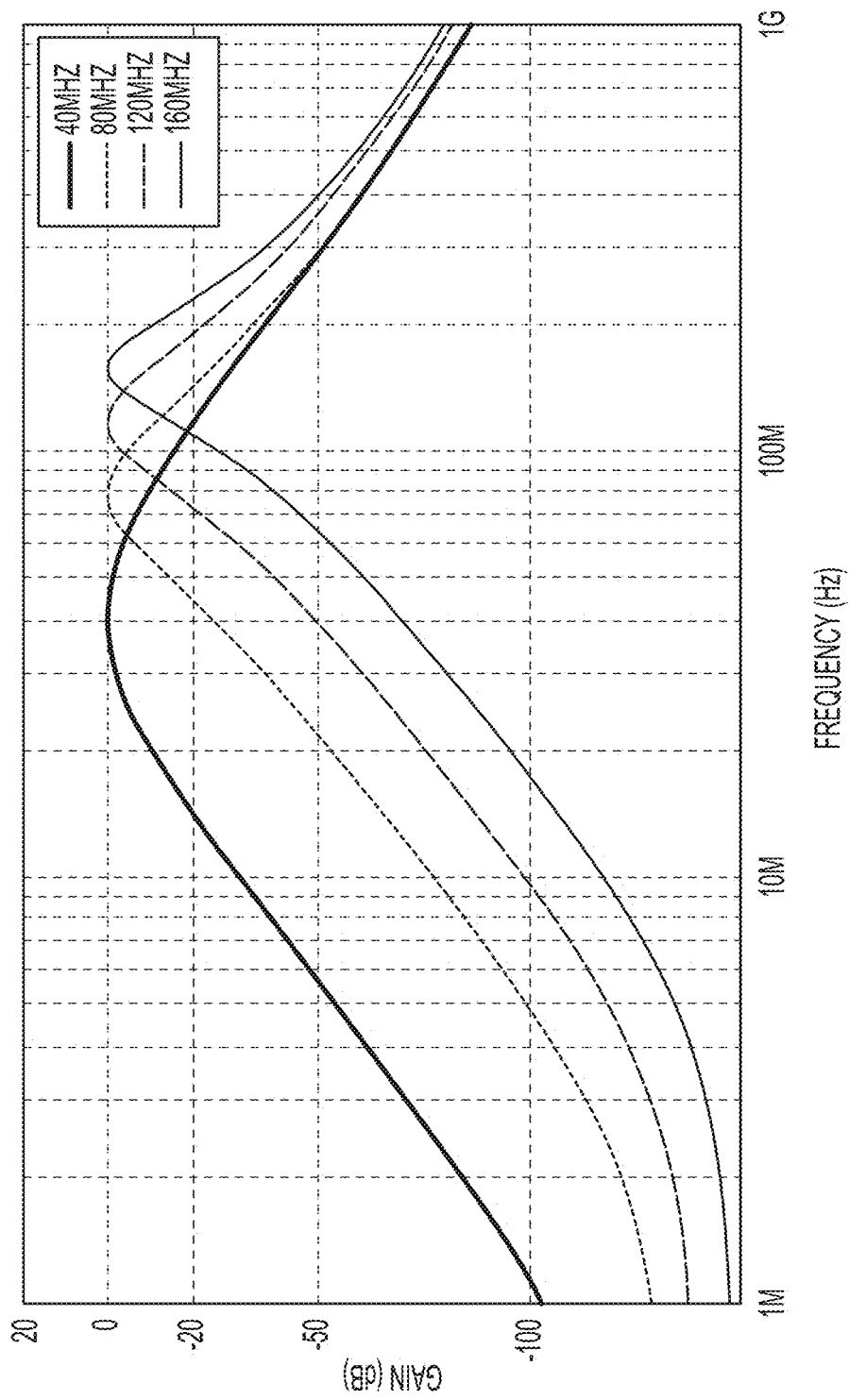
FIG. 18 illustrates a simulated frequency response of the designed band-pass filters.

A simulation of the OFDM multiplexing component 800 was performed in a CADENCE environment using Specter circuit simulation tool. Post layout simulation was performed of the individual blocks and the entire system. FIG. 15 shows the simulation result for the TIA 804 showing 89 dBΩ and bandwidth of 20 MHz, as designed for one example. To simulate the functionality to STD a 7 MHz center frequency 80% bandwidth Gaussian pulse was applied to the input which is shown in FIG. 16A. The outputs of the differential converter are shown in FIG. 16B, indicating close to the desired 180° phase shift. FIG. 17 illustrates the frequency response of the designed LPF 808 which has almost −80 dB/decade sharp roll off and 11 MHz bandwidth and FIG. 18 illustrates the frequency response of the designed BPFs 812. FIG. 18 illustrates that the center frequencies of the filters are 40 MHz, 80 MHz, 120 MHz and 160 MHz and bandwidth of each filter is ~30 MHz.

FIGS. 19A-19C illustrate some of the performance validation results of one example. To validate the performance of the analog OFDM and demodulation scheme the chip was first simulated with two 7 MHz 80% bandwidth Gaussian pulses shown FIG. 19A representing inputs from two channels. The two pulses were up-converted with orthogonal 40 MHz carriers shown FIG. 19B. The up-converted signals were de-modulated which are shown in FIG. 19C. It is clear from FIG. 19C that relative amplitude and phase of the signals were preserved.

Figure 20A:
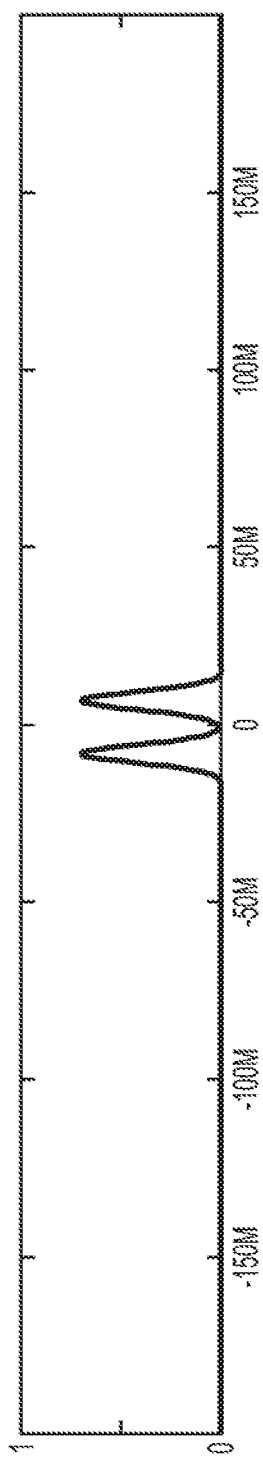
FIGS. 20A-20C illustrate a spectrum of 8 channel analog OFDM signals.
Figure 20B:
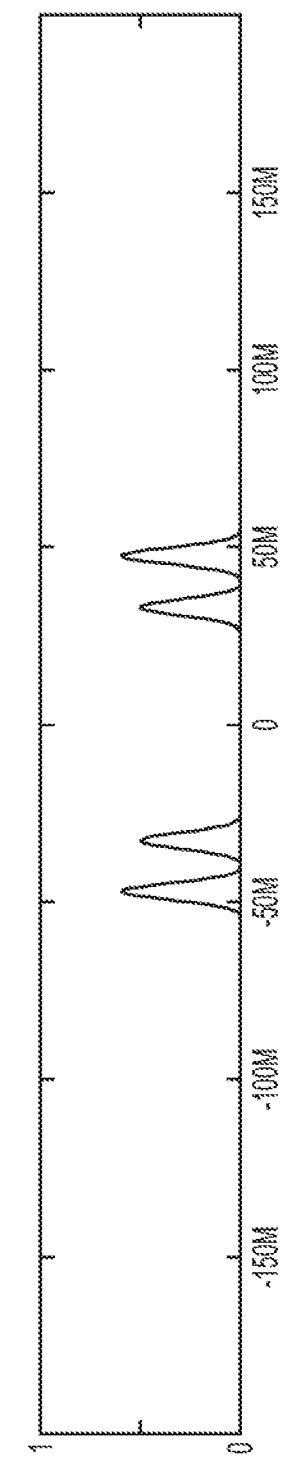
Figure 20C:
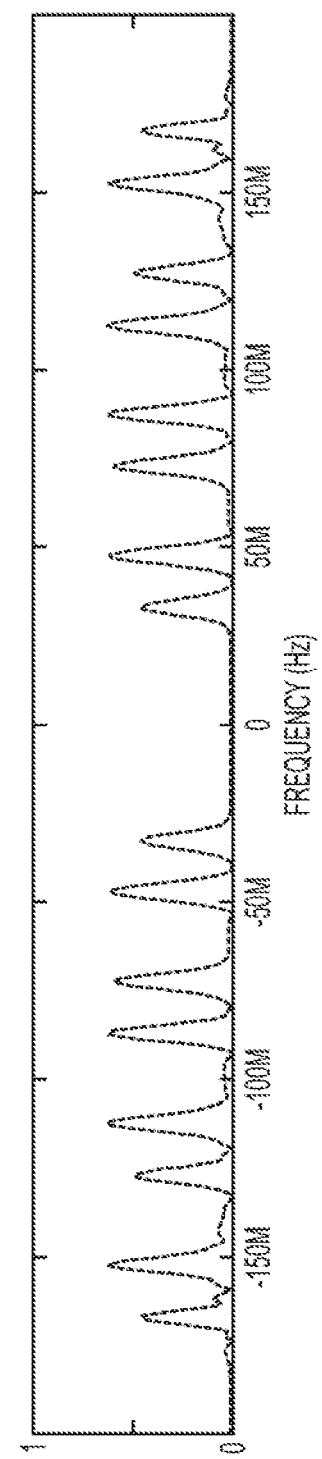

Although not detrimental, cross talk between the channels, lower than −20 dB, is also observed which may be due to the non-ideal single to differential, differential to single conversion or mixing. To verify the functionality of the entire designed chip 7 MHz 80% BW Gaussian pulses with different phase were applied to all 8 channels and modulated. FIG. 20A shows spectrum of a single channel input spectrum. FIG. 20B shows spectrum of two Gaussian pulses which are up-converted to 40 MHz. The spectrum of all the up-converted signals is shown in FIG. 20C. The spectra of the modulated signals are not identical to each other due to the different initial phases. During this simulation the total power consumed by the chip was ~160 mW.

While the present disclosure has been described in connection with a plurality of exemplary aspects, as illustrated in the various figures and discussed above, it is understood that other similar aspects can be used, or modifications and additions can be made to the described aspects for performing the same function of the present disclosure without deviating therefrom. For example, in various aspects of the disclosure, methods and compositions were described according to aspects of the presently disclosed subject matter. However, other equivalent methods or composition to these described aspects are also contemplated by the teachings herein. Therefore, the present disclosure should not be limited to any single aspect, but rather construed in breadth and scope in accordance with the appended claims.

What is claimed is:

1. An ultrasound imaging catheter comprising:
   a plurality of transmitters configured to transmit an imaging pulse;
   a plurality of receivers configured to receive the imaging pulse, at least a portion of the plurality of receivers configured to generate a receiver signal;
   a multiplexer configured to receive a number of the receiver signals simultaneously and configured to generate a number of output signals, based on the received receiver signals, the number of output signals being fewer than the number of received receiver signals; and
   a beamformer configured to communicate with at least a portion of the plurality of transmitters,
      wherein the ultrasound imaging catheter is compatible with magnetic resonance imaging ("MRI").

2. The catheter of claim 1, wherein the ratio of the number of receiver signals simultaneously received by the multiplexing component to the number of output signals is between 15-to-1 and 50-to-1.

3. The catheter of claim 1, wherein the catheter is visible with MRI.

4. The catheter of claim 3, wherein the ultrasound imaging catheter is visible with X-ray imaging.

5. The catheter of claim 1, further comprising at least one inductively or conductively coupled marker for catheter tracking with MRI.

6. The catheter of claim 1 further comprising a housing containing the plurality of transmitters, the plurality of receivers, the multiplexer, and the beamformer, wherein the housing is compatible with MRI.

7. The catheter of claim 6, further comprising output signal cables disposed within the housing, wherein the output signal cables are compatible with MRI.

8. The catheter of claim 1, wherein the multiplexing component produces the output signals using time division multiplexing ("TDM").

9. The catheter of claim 1, wherein the multiplexing component reduces the number of output signals, based on the receiver signals, by a ratio of at least 16-to-1.

10. The catheter of claim 1, further comprising a first capacitive micromachined ultrasonic transducer on complementary metal-oxide-semiconductor ("CMUT-on-CMOS") chip in which the plurality of transmitters, the plurality of receivers, the multiplexer, and the beamformer are integrated.

11. The catheter of claim 10, wherein the plurality of transmitters comprises capacitive micromachined ultrasonic transducer ("CMUT") transmitters; and
    wherein the plurality of receivers comprises CMUT receivers.

12. The catheter of claim 11, wherein the CMUT receivers are positioned proximate to the CMUT transmitters;
    wherein each CMUT receiver is configured to generate a receiver signal;
    wherein the multiplexer is configured to receive at least half of the generated receiver signals simultaneously and is configured to reduce a number of output signals, based on the received receiver signals, by a ratio of between 15-to-1 and 50-to-1; and
    wherein the beamformer is configured to communicate simultaneously with the CMUT transmitters.

13. The catheter of claim 1, wherein a first capacitive micromachined ultrasonic transducer on complementary metal-oxide-semiconductor ("CMUT-on-CMOS") chip comprises at least a portion of the plurality of transmitters and from none to all of the plurality of receivers;
    wherein a second CMUT-on-CMOS chip comprises a remainder of the plurality of transmitters and a remainder of the plurality of receivers;
    wherein the first CMUT-on-CMOS chip and the second CMUT-on-CMOS chip are oriented in a stacked configuration.

14. An intracardiac ultrasound echography catheter having an internal volume, a proximal end and a distal end, the catheter comprising:
    an atraumatic tip disposed approximate the distal end of the catheter;
    an inductively or conductively coupled marker for catheter tracking under magnetic resonance imaging ("MRI");
    a plurality of transmitters disposed proximal of the tip, the plurality of transmitters configured to transmit an imaging pulse;
    a plurality of receivers configured to receive the imaging pulse, and at least a portion of the plurality of receivers configured to generate a receiver signal;
    a multiplexer configured to receive at least a portion of the generated receiver signals simultaneously and produce a number of output signals, based on the received receiver signals, by a ratio of between 15-to-1 and 50-to-1;
    a beamformer configured to communicate with at least a portion of the plurality of transmitters; and
    a cable lumen disposed within the internal volume configured to receive output signal cables.

15. The catheter of claim 14, wherein the catheter is approximately 6 French to approximately 10 French.

16. The catheter of claim 14, wherein the catheter further comprises a cooling lumen configured to cool the catheter.

17. The catheter of claim 14, wherein the catheter further comprises:
- a first inductively coupled coil proximal to the atraumatic tip; and
- a second inductively coupled coil distal to the atraumatic tip,
- wherein the first and second coils are visible with MRI.

18. The catheter of claim 14, wherein the catheter further comprises:
- a body comprising at least one MRI compatible material; and
- a direction wire comprising at least one MRI compatible material disposed in a directional wire lumen,
- wherein the catheter is configured to be used during at least one of interlaced and simultaneous MRI and ultrasound operation.

19. The catheter of claim 14, wherein the multiplexer produces the number of output signals using time division multiplexing ("TDM").

20. The catheter of claim 14, wherein the catheter is visible with X-ray imaging.

* * * * *